United States Patent
Brooks et al.

(10) Patent No.: US 10,893,966 B2
(45) Date of Patent: Jan. 19, 2021

(54) CHECK VALVE WITH DOCKING STATION FOR GASTROINTESTINAL BALLOON

(71) Applicant: Spatz FGIA Ltd, Kfar Saba (IL)

(72) Inventors: Jeffrey Brooks, Ra'anana (IL); Sharon Dinar, Tel Aviv (IL)

(73) Assignee: SPATZ FGIA LTD, Kfar Saba (IL)

( * ) Notice: Subject to any disclaimer, the term of this patent is extended or adjusted under 35 U.S.C. 154(b) by 240 days.

(21) Appl. No.: 15/893,387

(22) Filed: Feb. 9, 2018

(65) Prior Publication Data

US 2018/0221184 A1    Aug. 9, 2018

Related U.S. Application Data

(60) Provisional application No. 62/457,056, filed on Feb. 9, 2017.

(51) Int. Cl.
*A61F 5/00* (2006.01)
*A61M 39/24* (2006.01)
(Continued)

(52) U.S. Cl.
CPC ............ *A61F 5/0043* (2013.01); *A61B 1/018* (2013.01); *A61B 1/2736* (2013.01);
(Continued)

(58) Field of Classification Search
CPC .. A61B 17/12136; A61F 5/003; A61F 5/0036; A61F 5/004; A61F 5/0043;
(Continued)

(56) References Cited

U.S. PATENT DOCUMENTS

| 3,726,283 A | 4/1973 | Dye et al. |
|---|---|---|
| 4,102,342 A | 7/1978 | Akiyama et al. |

(Continued)

FOREIGN PATENT DOCUMENTS

| CA | 1233387 A1 | 3/1988 |
|---|---|---|
| CA | 2068715 A1 | 2/1992 |

(Continued)

OTHER PUBLICATIONS

Andersen et al, "Randomised trial of endoscopic endoscopic endoprosthesis versus operative bypass in malignant obstructive jaundice", Gut, 30, 1132-1135 (1989).
(Continued)

*Primary Examiner* — Sarah A Simpson
(74) *Attorney, Agent, or Firm* — Venable LLP; Michele V. Frank

(57) ABSTRACT

A gastrointestinal balloon system includes a gastrointestinal balloon and a check valve located within the gastrointestinal balloon. The check valve is configured to allow fluid flow into and out of the gastrointestinal balloon. The check valve includes a string coupled to the check valve, the string having a loop on a proximal end and a catheter having a lumen. The lumen is configured to receive a grasping tool. The grasping tool extends out a distal end of the catheter for grabbing the loop to align the catheter with the check valve. Also, a check valve, two-wat valve, and method of using the same in a gastrointestinal balloon.

21 Claims, 26 Drawing Sheets

(51) Int. Cl.
*A61M 25/00* (2006.01)
*A61B 1/018* (2006.01)
*A61B 1/273* (2006.01)
*A61B 17/12* (2006.01)
*F16K 15/02* (2006.01)
*F16K 15/18* (2006.01)
*A61M 39/26* (2006.01)
*B25D 1/16* (2006.01)
*A61M 25/10* (2013.01)

(52) U.S. Cl.
CPC ........ *A61B 17/12013* (2013.01); *A61F 5/003* (2013.01); *A61F 5/0089* (2013.01); *A61M 25/0082* (2013.01); *A61M 39/24* (2013.01); *F16K 15/026* (2013.01); *A61B 17/12136* (2013.01); *A61M 25/10184* (2013.11); *A61M 39/26* (2013.01); *A61M 2025/1054* (2013.01); *A61M 2039/242* (2013.01); *A61M 2039/2473* (2013.01); *A61M 2039/267* (2013.01); *B25D 1/16* (2013.01); *F16K 15/18* (2013.01)

(58) Field of Classification Search
CPC .......... A61M 39/24; A61M 2025/1052; A61M 2025/1054
See application file for complete search history.

(56) References Cited

U.S. PATENT DOCUMENTS

| | | | |
|---|---|---|---|
| 4,116,201 A | 9/1978 | Shah | |
| 4,129,145 A | 12/1978 | Wynn | |
| 4,311,146 A | 1/1982 | Wonder | |
| 4,315,509 A | 2/1982 | Smit | |
| 4,416,267 A | 11/1983 | Garren et al. | |
| 4,447,227 A | 5/1984 | Kotsanis | |
| 4,485,805 A * | 12/1984 | Foster, Jr. ............... A61F 5/003 128/898 | |
| 4,598,699 A | 7/1986 | Garren et al. | |
| 4,694,827 A | 9/1987 | Weiner et al. | |
| 4,696,288 A | 9/1987 | Kuzmak et al. | |
| 4,738,667 A | 4/1988 | Galloway | |
| 4,739,758 A | 4/1988 | Lai et al. | |
| 4,766,628 A | 8/1988 | Walker | |
| 4,813,934 A | 3/1989 | Engelson et al. | |
| 4,878,905 A | 11/1989 | Blass | |
| 4,899,747 A | 2/1990 | Garren et al. | |
| 4,908,011 A | 3/1990 | Jacobsen et al. | |
| 4,925,446 A * | 5/1990 | Garay ..................... A61F 5/003 128/899 | |
| 5,002,556 A * | 3/1991 | Ishida ............. A61B 17/12109 604/103.1 | |
| 5,052,998 A | 10/1991 | Zimmon | |
| 5,084,061 A | 1/1992 | Gau et al. | |
| 5,129,915 A | 7/1992 | Cantenys | |
| 5,167,239 A | 12/1992 | Cohen et al. | |
| 5,234,454 A | 8/1993 | Bangs | |
| 5,259,399 A | 11/1993 | Brown | |
| 5,380,282 A | 1/1995 | Burns | |
| 5,433,216 A | 7/1995 | Sugrue et al. | |
| 5,458,583 A | 10/1995 | McNeely et al. | |
| 5,536,274 A | 7/1996 | Neuss | |
| 5,578,048 A | 11/1996 | Pasqualucci et al. | |
| 5,624,395 A | 4/1997 | Mikhail et al. | |
| 5,724,994 A | 3/1998 | Simon et al. | |
| 5,732,715 A | 3/1998 | Jacobs et al. | |
| 5,827,304 A | 10/1998 | Hart | |
| 5,976,106 A | 11/1999 | Verin et al. | |
| 5,985,307 A | 11/1999 | Hanson et al. | |
| 6,050,972 A | 4/2000 | Zadno-Azizi et al. | |
| 6,127,597 A | 10/2000 | Beyar et al. | |
| 6,183,461 B1 | 2/2001 | Matsuura et al. | |
| 6,213,936 B1 | 4/2001 | Nishioka et al. | |
| 6,245,040 B1 | 6/2001 | Inderbitzen et al. | |
| 6,364,686 B2 | 4/2002 | Gimbel | |
| 6,364,868 B1 | 4/2002 | Ikeguchi | |
| 6,569,173 B1 | 5/2003 | Blatter et al. | |
| 6,616,678 B2 | 9/2003 | Nishtala et al. | |
| 6,652,339 B1 | 11/2003 | Carmichael | |
| 6,656,194 B1 | 12/2003 | Gannoe et al. | |
| 6,712,831 B1 | 3/2004 | Kaplan et al. | |
| 6,743,198 B1 | 6/2004 | Tihon | |
| 6,746,460 B2 | 6/2004 | Gannoe et al. | |
| 7,004,176 B2 | 2/2006 | Lau | |
| 7,033,384 B2 | 4/2006 | Gannoe et al. | |
| 7,056,305 B2 | 6/2006 | Garza Alvarez | |
| 7,087,009 B2 | 8/2006 | Migachyov | |
| 7,147,665 B1 | 12/2006 | Bryan et al. | |
| 7,331,949 B2 | 2/2008 | Marisi | |
| 7,347,868 B2 | 3/2008 | Burnett et al. | |
| 7,470,251 B2 | 12/2008 | Shah | |
| 7,628,821 B2 | 12/2009 | Stack et al. | |
| 7,654,950 B2 | 2/2010 | Yachia et al. | |
| 7,753,928 B2 | 7/2010 | de la Torre et al. | |
| 7,883,524 B2 | 2/2011 | Chen | |
| 8,062,207 B2 | 11/2011 | Gannoe et al. | |
| 8,088,103 B2 | 1/2012 | Teeslink et al. | |
| 8,403,952 B2 | 3/2013 | Brooks et al. | |
| 8,888,739 B2 | 11/2014 | Gregory et al. | |
| 8,939,991 B2 | 1/2015 | Krolik et al. | |
| 9,044,571 B2 | 6/2015 | Pinchuk et al. | |
| 9,308,361 B2 | 4/2016 | Muni et al. | |
| 9,399,121 B2 | 7/2016 | Goldfarb et al. | |
| 9,504,811 B2 | 11/2016 | Tilson et al. | |
| 9,974,680 B2 * | 5/2018 | Brooks ................. A61F 5/0089 | |
| 2001/0020150 A1 | 9/2001 | Ravo | |
| 2002/0045914 A1 | 4/2002 | Roberts et al. | |
| 2002/0055757 A1 | 5/2002 | Torre et al. | |
| 2002/0151923 A1 | 10/2002 | Holzer | |
| 2003/0158569 A1 | 8/2003 | Wazne | |
| 2003/0171768 A1 | 9/2003 | McGhan | |
| 2003/0191492 A1 | 10/2003 | Gellman et al. | |
| 2004/0030347 A1 | 2/2004 | Gannoe et al. | |
| 2004/0044357 A1 | 3/2004 | Gannoe et al. | |
| 2004/0059289 A1 | 3/2004 | Garza Alvarez | |
| 2004/0064893 A1 | 4/2004 | Sharp | |
| 2004/0088008 A1 | 5/2004 | Gannoe et al. | |
| 2004/0093091 A1 | 5/2004 | Gannoe et al. | |
| 2004/0167625 A1 | 8/2004 | Beyar et al. | |
| 2004/0193092 A1 | 9/2004 | Deal | |
| 2004/0225247 A1 | 11/2004 | Pugsley et al. | |
| 2004/0267378 A1 | 12/2004 | Gazi et al. | |
| 2005/0004430 A1 | 1/2005 | Lee et al. | |
| 2005/0033331 A1 | 2/2005 | Burnett et al. | |
| 2005/0033345 A1 | 2/2005 | DeLegge | |
| 2005/0055039 A1 | 3/2005 | Burnett et al. | |
| 2005/0070937 A1 | 3/2005 | Jambor et al. | |
| 2005/0085923 A1 | 4/2005 | Levine et al. | |
| 2005/0096750 A1 | 5/2005 | Kagan et al. | |
| 2005/0125020 A1 | 6/2005 | Meade et al. | |
| 2005/0192614 A1 | 9/2005 | Binmoeller | |
| 2005/0192629 A1 | 9/2005 | Saadat et al. | |
| 2005/0209674 A1 | 9/2005 | Kutscher et al. | |
| 2005/0216040 A1 | 9/2005 | Gertner et al. | |
| 2005/0228504 A1 | 10/2005 | Demarais | |
| 2005/0256460 A1 | 11/2005 | Rome et al. | |
| 2005/0267361 A1 | 12/2005 | Younker et al. | |
| 2005/0267595 A1 | 12/2005 | Chen et al. | |
| 2005/0267596 A1 | 12/2005 | Chen et al. | |
| 2006/0020278 A1 | 1/2006 | Burnett et al. | |
| 2006/0058892 A1 | 3/2006 | Lesh et al. | |
| 2006/0100479 A1 | 5/2006 | Yachia et al. | |
| 2006/0142731 A1 | 6/2006 | Brooks | |
| 2006/0190019 A1 | 8/2006 | Gannoe et al. | |
| 2006/0206064 A1 | 9/2006 | Kagan et al. | |
| 2006/0271088 A1 | 11/2006 | Alfrhan | |
| 2007/0083224 A1 | 4/2007 | Hively | |
| 2007/0088380 A1 | 4/2007 | Hirszowicz et al. | |
| 2007/0118168 A1 | 5/2007 | Lointier et al. | |
| 2007/0149994 A1 | 6/2007 | Sosnowski et al. | |
| 2007/0173881 A1 * | 7/2007 | Birk ..................... A61F 5/0036 606/192 | |
| 2007/0239284 A1 | 10/2007 | Skerven et al. | |

(56) References Cited

U.S. PATENT DOCUMENTS

| | | | |
|---|---|---|---|
| 2008/0147012 A1 | 6/2008 | Rome | |
| 2008/0172079 A1* | 7/2008 | Birk | A61F 5/0036 606/192 |
| 2008/0208135 A1 | 8/2008 | Annunziata | |
| 2009/0152379 A1 | 6/2009 | Harter | |
| 2009/0164028 A1 | 6/2009 | Chen | |
| 2009/0171382 A1 | 7/2009 | Dillon et al. | |
| 2009/0287231 A1 | 11/2009 | Brooks et al. | |
| 2010/0121371 A1 | 5/2010 | Brooks et al. | |
| 2010/0252464 A1 | 10/2010 | Belitz | |
| 2010/0274189 A1 | 10/2010 | Kurth et al. | |
| 2011/0092998 A1 | 4/2011 | Hirszowicz et al. | |
| 2011/0218563 A1 | 9/2011 | Brooks et al. | |
| 2012/0191123 A1 | 7/2012 | Brister et al. | |
| 2012/0296365 A1 | 11/2012 | Nguyen | |
| 2013/0035710 A1 | 2/2013 | Bouasaysy et al. | |
| 2013/0255807 A1 | 10/2013 | Bonzon et al. | |
| 2014/0249374 A1 | 9/2014 | Evans et al. | |
| 2016/0100946 A1 | 4/2016 | Fogarty et al. | |
| 2016/0193064 A1 | 7/2016 | Brister et al. | |
| 2016/0310306 A1 | 10/2016 | Brister et al. | |
| 2017/0007310 A1 | 1/2017 | Rajagopalan et al. | |
| 2017/0156909 A1* | 6/2017 | Brister | A61F 5/0089 |
| 2017/0325982 A1 | 11/2017 | Brooks et al. | |
| 2017/0354437 A1 | 12/2017 | Bacich | |
| 2018/0209553 A1* | 7/2018 | Weaver | A61M 39/24 |
| 2018/0221184 A1 | 8/2018 | Brooks et al. | |

FOREIGN PATENT DOCUMENTS

| | | |
|---|---|---|
| CA | 2483335 A1 | 3/2005 |
| DE | 3227585 A1 | 5/1983 |
| DE | 3326061 A1 | 2/1984 |
| DE | 3310234 A1 | 9/1984 |
| DE | 3540936 C1 | 10/1986 |
| EP | 246999 A1 | 11/1987 |
| EP | 1342458 B1 | 8/2005 |
| EP | 2004269 B1 | 8/2016 |
| GB | 2090747 A | 7/1982 |
| GB | 2139902 A | 11/1984 |
| IT | 1235492 B | 9/1992 |
| JP | 2008517677 A | 5/2008 |
| WO | 1986006611 A1 | 11/1986 |
| WO | 1987000034 A2 | 1/1987 |
| WO | 1998056321 A1 | 12/1998 |
| WO | 2001066166 A2 | 9/2001 |
| WO | 2002040081 A2 | 5/2002 |
| WO | 2003055420 A1 | 7/2003 |
| WO | 2003095015 A1 | 11/2003 |
| WO | 2004014237 A1 | 2/2004 |
| WO | 2004089262 A2 | 10/2004 |
| WO | 2004105622 A1 | 12/2004 |
| WO | 2005009288 A2 | 2/2005 |
| WO | 2005039457 A1 | 5/2005 |
| WO | 2005107641 A2 | 11/2005 |
| WO | 2005094257 A3 | 1/2006 |
| WO | 2006047708 A2 | 5/2006 |
| WO | 2007110866 A3 | 10/2007 |
| WO | 2008042819 A2 | 4/2008 |
| WO | 2008132745 A2 | 11/2008 |
| WO | 2006070361 A3 | 4/2009 |
| WO | 2011041864 A1 | 4/2011 |
| WO | 2011097636 A1 | 8/2011 |
| WO | 2016/200612 A1 | 12/2016 |
| WO | 2018146547 A1 | 8/2018 |

OTHER PUBLICATIONS

Borowski A et al., "Minimally Invasive, Nonendoscopic Saphenectomy for Coronary Bypass Surgery", J Card Surg 16 (6): 484-6, (2001)—an abstract.

Cope, "Improved Anchoring of Nephrostomy Catheters: Loop Technique", American J of Roetngenology 1980.

Dondelinger et al, "Percutaneous management of intraperitoneal, hepatic and other fluid collections", Baillieres Clin Gastroenterol (1992).

Dumon, J.R. et al., "A new method of esophageal dilation using Savary-Gilliard Bougies," Gastro Endosc 31:379-82, 1985.

Fleischer, D.E. et al., "A marked guidewire facilitates esophageal dilation," Am J Gastro 84:359-61, 1989.

Gronval et al , "Ultrasound-guided Drainage of Fluid-containing Masses Using Angiographic Catheterization Techniques", Am J Roetgenol (1977).

Kadakia, SC et al., "Esophageal dilation with polyvinyl bougies using a marked guidewire without the aid of fluoroscopy," Am J Gastro 88:1381-86, 1993.

Lambiase, "Percutaneous Abscess and Fluid Drainage: A Critical Review", Cardiovascular and interventional radiology 14: 143-157 (1991).

Parker et al. "Esophageal dilation with polyvinyl bougies, using a marked guidewire without the aid of fluoroscopy: an update", Am J Gastroenterol. (Sep. 1993); 88(9):1381-6—an abstract.

Shepherd et al, "Endoscopic biliary endoprosthesis in the palliation of malignant obstruction of the distal common bile duct: a randomized trial", British journal of surgery, vol. 75, pp. 1166-1168 (1988).

Speer et al, "Randomised Trial of Endoscopic Versus Percutaneous Stent Insertion in Malignant Obstructive Jaundice", The Lancet (1987).

Van sonnenberg et al, "Percutaneous Abscess Drainage: Current Concepts", Radiology (1991).

Werth, et al., "A safe and quick method for endoscopic retrieval of multiple gastric foreign bodies using a protective sheath," Surg Gynecol Obstet 171(5):419-20, 1990.

CN200580048692.6: English Translation of an Office Action dated Apr. 13, 2010.

EP07736138: European Search Report (Supplementary) dated Jul. 26, 2013.

EP11161677.7: European Search Report dated Aug. 22, 2011.

IL183649: Office Action dated Jan. 21, 2010, and English translation.

JP548959/2007: Office Action dated Apr. 26, 2011, and English translation.

JP2009-502330: Office Action dated Feb. 17, 2012.

JP2011-056619: Office Action dated Oct. 16, 2012.

PCT/IL05/01381: International Search Report dated May 28, 2008.

PCT/IL07/00398: International Search Report dated Sep. 22, 2008.

PCT/IL08/00579: International Search Report dated Dec. 23, 2008.

PCT/IL10/00833: International Search Report dated Feb. 10, 2011.

PCT/US2013/071730: International Search Report and Written Opinion dated Mar. 10, 2014.

U.S. Appl. No. 11/132,855: Office Action dated Oct. 16, 2008.

U.S. Appl. No. 11/132,855: Office Action dated Jun. 11, 2009.

U.S. Appl. No. 11/132,855: Office Action dated Dec. 30, 2009.

U.S. Appl. No. 11/132,855: Office Action dated Jun. 25, 2010.

U.S. Appl. No. 11/132,855: Office Action dated Aug. 24, 2011.

U.S. Appl. No. 11/132,855: Office Action dated Mar. 27, 2012.

U.S. Appl. No. 11/718,795,: Office Action dated Sep. 17, 2010.

U.S. Appl. No. 11/721,993: Office Action dated Feb. 27, 2012.

U.S. Appl. No. 12/598,110: Office Action dated Dec. 13, 2011.

U.S. Appl. No. 12/903,448: Office Action dated Sep. 18, 2012.

U.S. Appl. No. 60/639,843.

U.S. Appl. No. 60/787,124.

U.S. Appl. No. 60/815,624.

Indian Examination Report issued in corresponding Indian Application No. 9024/DELNP/2008 dated Jan. 27, 2017 (9 pages).

U.S. Appl. No. 62/457,056.

International Search Report and Written Opinion dated Jul. 12, 2018 in corresponding International Application No. PCT/IB18/00173 (9 pages).

Office Action issued in U.S. Appl. No. 12/598,110 dated Nov. 7, 2013.

International Search Report and Written Opinion issued in related International Patent Application No. PCT/US2019/067921 dated Mar. 10, 2020.

Office Action issued in U.S. Appl. No. 15/949,342 dated Apr. 17, 2020.

(56) References Cited

OTHER PUBLICATIONS

Office Action issued in U.S. Appl. No. 11/718,795 dated Jul. 8, 2011.
Office Action issued in U.S. Appl. No. 11/718,795 dated Oct. 9, 2012.
Office Action issued in U.S. Appl. No. 14/647,372 dated Oct. 2, 2017.
Office Action issued in related Indian Patent Application No. 9024/DELNP/2008 dated Nov. 5, 2019.
Extended European Search Report for European Application No. 18751369.2 dated Dec. 1, 2020.

* cited by examiner

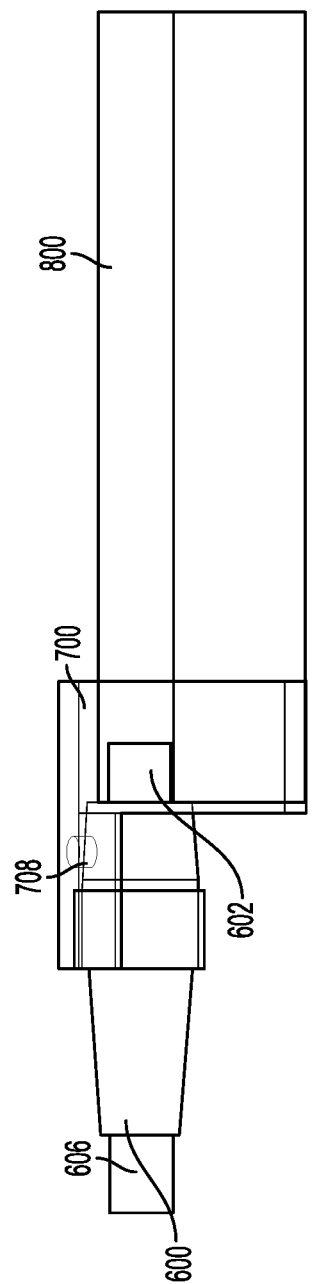

CHECK VALVE WITH DOCKING STATION FOR GASTROINTESTINAL BALLOON

CROSS-REFERENCE TO RELATED APPLICATIONS

This application claims priority to U.S. Provisional Application No. 62/457,056, filed Feb. 9, 2017, the disclosure of which is incorporated herein by reference in its entirety.

TECHNICAL FIELD OF THE INVENTION

The present invention relates generally to implantable medical devices and systems that include a check valve, and methods of using implantable medical devices and systems with a check valve. Specifically, the present invention relates to devices, systems, and methods for a check valve and a gastrointestinal balloon including a check valve. The present invention also relates generally to a check valve with docking station. The check valve with docking station may be in a remote location or a difficult to access locations.

BACKGROUND OF THE INVENTION

Morbid obesity remains an ever-growing problem in the U.S. Varying forms of gastric bypass surgery have developed and have improved over the last few decades. Recently, laparoscopic gastric bypass has emerged as a less invasive surgical option. However, bariatric surgery is fraught with morbidity of up to 20%, with a re-operation rate approaching 25% at 3-5 years post-operation. Bariatric surgery carries an operative mortality of 0.5%. Diet and pharmaceutical alternatives have not been very effective, with a high recidivism rate. Intragastric balloons in use may achieve weight loss and a drop in body mass index (BMI). However, it is desirable to be able to change the volume of the balloon while in the stomach of a patient, either to increase the balloon volume or decrease the balloon volume, as balloon effect wears off after several months and enlarging the balloon can rejuvenate the balloon effect, and some balloons may cause intolerance and require balloon volume decrease.

There is a need to be able to change the volume of a gastrointestinal balloon while the balloon is in the stomach of a patient. In order to access the balloon valve to adjust balloon volume while the balloon is still in the stomach, there are two options. One option is to bring the valve out of the stomach to the mouth of a patient, where balloon volume may be manually adjusted. For example, some existing gastrointestinal balloon systems use a stretchable inflation tube that may stretch from a stomach to the mouth of the patient, or about 2.5-10 times its length, to facilitate inflation or adjustment of volume of the balloon. The inflation tube is partly inside and partly outside of the balloon. U.S. Patent Application Publication No. 2006/0142731 and U.S. Pat. No. 8,403,952, which are incorporated herein by reference, describe a floating anchor that may be used, for example, with the gastrointestinal balloon. However, further improvements may be made to limit side effects from implantable devices including, but not limited to, tissue trauma, difficulty finding the tube, and difficulty grasping the tube, some of which may result of components of the devices that are located on the outside of the gastrointestinal balloon.

Another option is to keep the valve stationary in the balloon and access the valve itself while the valve resides in the stomach, without removing any of the components from the stomach. However, direct access to the balloon valve while the valve is within the stomach via an endoscope is extremely difficult and may not be feasible because the positioning of the endoscope relative to the balloon valve requires pinpoint precision with head-on engagement. This is a technically difficult maneuver for an endoscope engaging a spherical balloon in the wet environment of the stomach. For example, the balloon may easily move within the stomach while, or as a result of, attempting to engage the valve.

Thus, there exists a need for improved gastrointestinal balloon devices, systems, and methods for accessing a balloon valve while it is in the stomach in a way that provides a high success rate for engaging with the valve to adjust the balloon volume.

BRIEF SUMMARY OF THE INVENTION

According to embodiments of the invention, a gastrointestinal balloon is immobilized within the stomach to improve the ease of engaging the valve. In particular, the balloon may be immobilized while at the same time allowing access to the valve at the correct angle by the inflation tool. A check valve is a type of valve that may be used for changing the volume of a gastrointestinal balloon. However, a standard check valve cannot be simultaneously immobilized and accessed with current check valve configurations and technology.

Thus, novel devices, systems, and methods are provided herein for a check valve used in inflatable medical devices, including but not limited to gastrointestinal balloons that may be simultaneously immobilized and accessed while in a body cavity. After immobilization of the balloon and aligning of the inflation tool to the balloon valve, the balloon may be inflated or deflated.

Additional features, advantages, and embodiments of the invention are set forth or apparent from consideration of the following detailed description and drawings. Moreover, it is to be understood that both the foregoing summary of the invention and the following detailed description are exemplary and intended to provide further explanation without limiting the scope of the invention as claimed.

According to an embodiment of the present disclosure, a check valve for use in a gastrointestinal balloon may include a housing having an entry, the entry configured to allow fluid flow into and out of the gastrointestinal balloon; a plunger configured to open and close the entry; and an attachment extending from a proximal end of the housing. The attachment is configured to be grasped by a tool to permit aligning of a catheter with a proximal end of the housing.

The check valve includes an open position and a closed position, wherein the check valve is configured to be moved to the open position in a stomach. The check valve is configured to be mobile in a stomach. The catheter is configured to impact the proximal end of the housing. The plunger further comprising a plunger head, a plunger arm, and a plunger tail. The plunger head includes an opening for the attachment to extend through and a seal for sealing the opening. The plunger arm is formed from a cylindrical body with two semi-circular arms extending between the cylindrical body and a distal end of the plunger head. The plunger tail is coupled to a distal end of the plunger arm. The plunger head, plunger arm, and plunger tail are integrally formed as a single unit. An o-ring seal is located between the plunger arm and the plunger tail. A block is coupled to the housing and coupled to the attachment. A spring is coupled between the block and a proximal end of the housing. An opening in the proximal end of the housing is configured to removably receive a distal end of the catheter.

According to an embodiment of the present disclosure, a gastrointestinal balloon system, may include a gastrointestinal balloon; a valve located within the gastrointestinal balloon, the valve configured to allow fluid flow into and out of the gastrointestinal balloon; an attachment coupled to the valve, the attachment having a connector on a proximal end; and a shaft having a lumen, the lumen configured to receive a grasping tool. The grasping tool extends out a distal end of the shaft for grabbing the connector to align the shaft with the valve.

The shaft is a catheter and the catheter has a tapered distal tip. The valve separates an interior of the gastrointestinal balloon with an exterior of the gastrointestinal balloon. The gastrointestinal balloon is configured to be inflated or deflated through the valve. The valve includes a proximal opening, a plunger, and an o-ring to seal an entry into the gastrointestinal balloon. The valve is a check valve. The attachment is a string.

According to an embodiment of the present disclosure, a method of accessing a gastrointestinal balloon may include inserting a catheter through a channel of a gastroscope and into a stomach of a patient; inserting a grasping tool through a lumen of the catheter and extending the grasping tool through a distal end of the catheter; grasping an attachment with the grasping tool, wherein the attachment is coupled to a check valve; moving the check valve into alignment with the catheter; moving a plunger in the check valve such that the check valve is moved from a closed position to an open position; and inflating or deflating the gastrointestinal balloon through the check valve.

The method includes removably impacting the catheter into the check valve. The method includes impacting the catheter into the check valve comprises impacting a distal end of the catheter with a proximal opening of a housing of the check valve. The method includes moving the plunger in the check valve comprises distally moving the plunger in the check valve. The method includes releasing the attachment from the grasping tool and removing the grasping tool from the catheter prior to inflating or deflating the gastrointestinal balloon. The distal end of the catheter is tapered.

According to an embodiment of the present disclosure, a check valve system may include a check valve having a housing, the housing having a distal opening and a proximal opening, the distal opening configured to be sealed; an elongated member coupled to the housing, the elongated member having a proximal end with a connector; a tool configured to grasp the connector; and an impacting member configured to engage a proximal end of the housing. The tool is inserted through the impacting member to grasp the connector to align and immobilize the check valve with the impacting member. The tool is subsequently pulled to engage the impacting member into the proximal end of the housing to open the distal opening of the check valve. The check valve is configured for installation in a stomach, in a pipeline, in a plumbing line, or in a body cavity. A spring is configured to bias the check valve to a closed position.

According to an embodiment of the present disclosure, a two-way valve may include a body configured to allow two-way flow. The body may have a docking end configured to receive a tool for positioning the body in a first position; and a port end configured to be disposed in a cavity. The valve has the first position and a second position. The docking end further includes an attachment to align the tool with the docking end.

The first position is an open configuration and the second position is a closed configuration, the valve biased to the second position. The two-way valve is a check valve. The attachment is a strap. The docking end comprises an opening in a proximal end of the body. The opening is configured to receive the tool for releasably impacting the plunger.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 13 shows the biluminal connector and coupling sleeve of FIG. 12 coupled to a gastroscope, according to an embodiment of the present disclosure.

DETAILED DESCRIPTION OF THE INVENTION

Devices, systems and methods are described herein with reference to the figures and in the context of medical devices, in particular a gastric balloon. In one aspect, a check valve with docking station can be provided to improve the ability to control the check valve for purposes of adjusting a gastric balloon (such as inflating and deflating the balloon). The check valve with docking station can improve the user's ability to change the volume of a gastrointestinal balloon while the balloon is in the stomach of a patient. The check valve with docking station can be used in other environments in order to access and adjust the valve in hard to reach areas where the devices may or may not be stabilized. The check valve docking features can be implement in other medical devices as well as non-medical devices and used as described herein in accordance with the principles of the invention. The check valve may include a plunger, string, spring, and valve housing. The string may be coupled to the housing such that when grasped and pulled, it aligns an opening of the valve housing with an impacting member for operating the opening and closing of the valve. Thus, the valve may be controlled from a remote location to allow fluid to flow into or out of the valve, as will be appreciated from the disclosure to follow.

Figure 1:
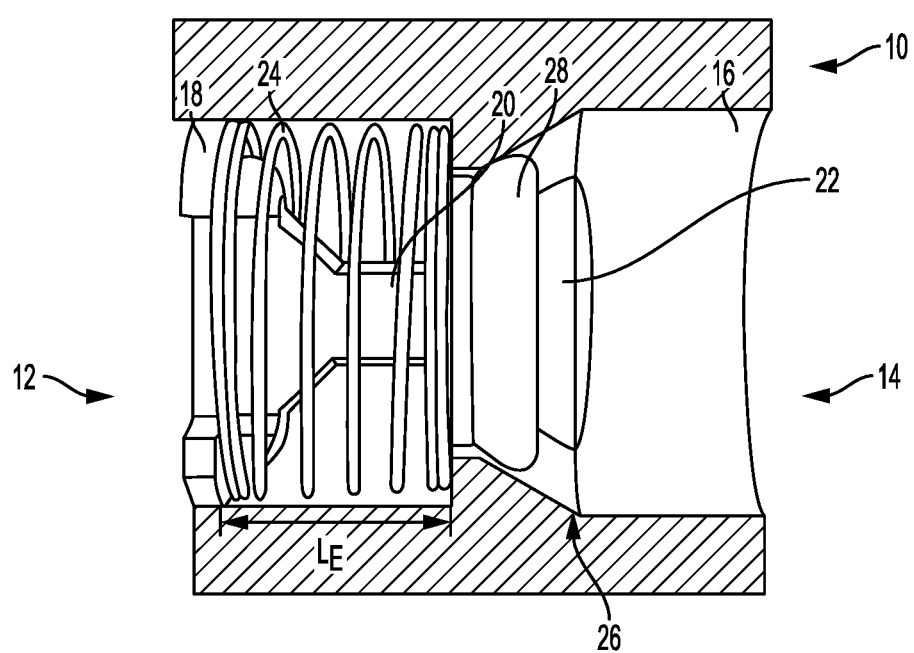
FIG. 1 shows a standard check valve attached to a balloon, with the valve in the closed position.
Figure 2:
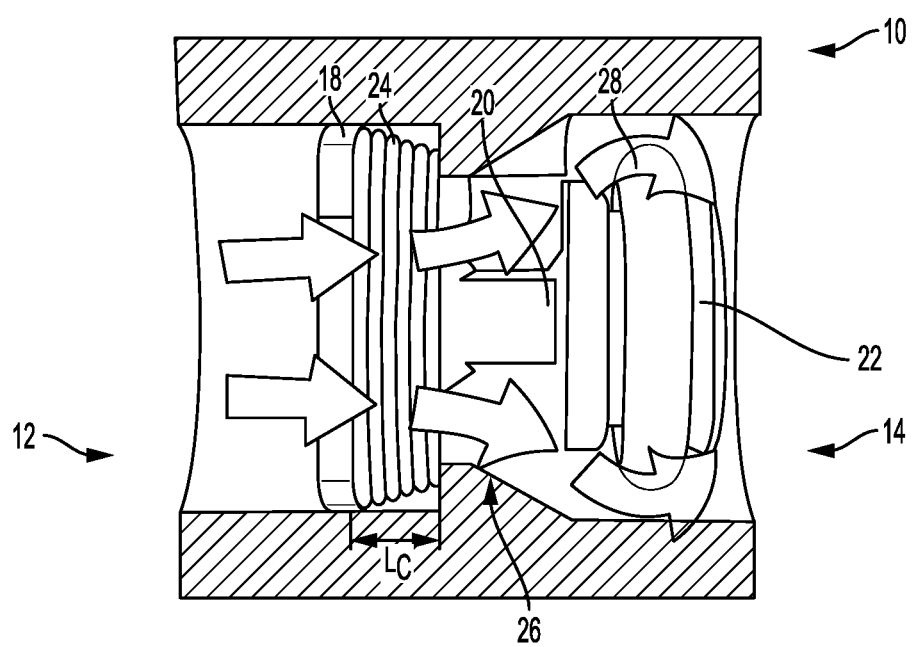
FIG. 2 shows the standard check valve of FIG. 1, with the valve in the open position.

A standard check valve 10, as shown in FIGS. 1 and 2 (in the closed and opened positions, respectively), cannot be simultaneously immobilized and accessed with current check valve configurations and technology. FIGS. 1 and 2 depict a check valve 10 which separates the exterior 12 of the balloon from the interior or cavity 14 of the balloon. The check valve 10 may include a housing 16, plunger head 18, plunger arm 20, and a plunger tail 22. In FIG. 1, a spring 24, at a full extension length $L_E$, keeps the check valve 10 in a closed position by pushing plunger head 18 away (to the left in the view shown in FIG. 1) from the mouth or entry 26 into the balloon cavity 14. The plunger head 18 in turn pulls the plunger arm 20 and the plunger tail 22 to the left and closes the entry 26 into the balloon cavity 14 by pulling an o-ring 28 to the left. In FIG. 2, The plunger head 18 is pushed toward (to the right in the view shown in FIG. 2) the entry 26 which contracts the spring 24 to a length $L_C$, thereby allowing the plunger head 18 to move to the right (FIG. 2) towards the balloon cavity entry 26. The plunger head 18 then pushes the plunger arm 20 and the plunger tail 22 to the right which pushes the o-ring 28 to the right and opens for the bi-directional flow of fluid (arrows F) into and out of the balloon cavity 14.

Engaging the check valve 10 in the balloon while the check valve 10 sits in the body cavity (e.g. the stomach) requires some method of immobilization and proper alignment of a tool on the check valve 10 of the balloon, followed by applying force to push the spring 24 towards the balloon cavity 14 (thereby opening flow F to the balloon cavity 14). Therefore, the present invention provides a novel modification to check valve technology that may accomplish these goals. The novel check valve has utility not only in the intragastric adjustable balloon, but also in other inflatable medical devices in any body cavity or check valves for industrial and non-medical use, such as in plumbing. Therefore, references to "gastrointestinal balloons" or "stomach" are for example only, and are not intended to limit the scope of the invention.

Figure 3:
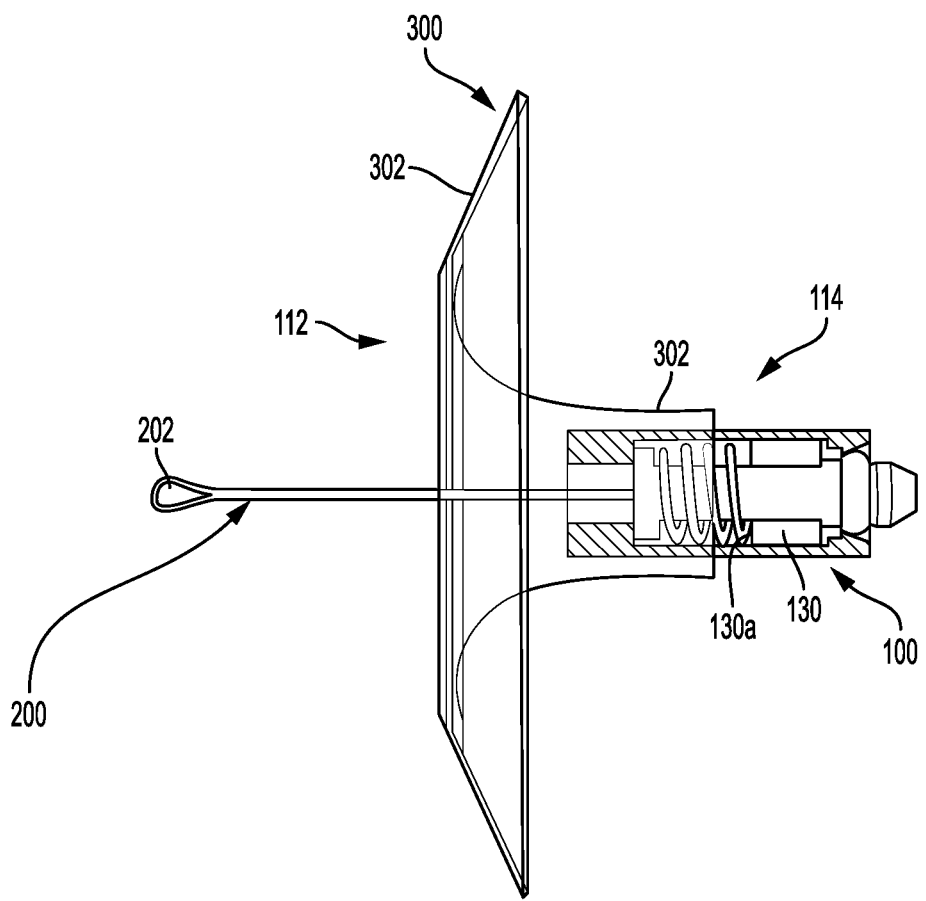
FIG. 3 shows a check valve in a gastrointestinal balloon according to an embodiment of the present invention.

FIG. 3 shows a valve 100 according to an embodiment of the invention. The valve 100 may be a check valve, two-way valve, two directional flow valve, or other valve having an opening configured to be selectively opened and closed in accordance with the principle of the invention. For ease of description, the valve 100 is referred to herein as a check valve 100. The check valve 100 may include a docking station to allow for alignment and engagement of an impacting member to open and close the check valve 100. The check valve 100 is shown within a balloon 300 or integral with a sidewall 302 of the balloon 300. The balloon 300 may be an adjustable balloon located in a patient's stomach. Alternatively, the check valve 100 may be located in a flow line of a plumbing or other hydraulic system. The balloon 300 may have an interior cavity 114 separated from an exterior space 112 (e.g. the stomach environment). The check valve 100 may separate the interior cavity 114 of the balloon 300 from the exterior space 112 of the balloon 300. The check valve 100 may be provided with an attachment 200, such as an elongated member 200, such as a string 200 that may be have a connector 202. The connector 202 may be an "easy grasp" loop 202 that exits into the exterior space 112 of the balloon 300. The string 200 with easy grasp loop 202 may be formed of nylon. The attachment 200 may be an elongated member, a bungee, a stretchy member, a string, a cable, a cord, other elongated device, or anything in accordance with the principles of invention capable of coupling to the check valve 100 and being grasped by a tool. For ease of description, the attachment 200 is described as a string 200 and the connector 202 is described as a loop 202. The string 200 may be a single string 200 having opposing distal ends, each coupled to a block 130 (FIG. 4) of the housing of the check valve 100 with the easy grasp loop 202 formed therebetween.

Moving (e.g. by pulling or pushing the impacting member and/or tool) the loop 202 into an impacting member 400 (FIG. 7), such as a catheter, may immobilize the balloon 300 and may guide the inflation/pushing catheter (not depicted) to the target (i.e., the check valve 100), as will be described to follow. The string 200 may have a proximal end having a loop (such as easy grasp loop 202) configured to be grasped be a tool. The easy grasp loop 202 may be pulled into a catheter by a grasping tool dispatched through an endoscope, as will be described in more detail. As may be appreciated, the balloon 300 may be located in a patient's stomach. The balloon 300 (including check valve 100) may be floating or otherwise mobile within the stomach as the balloon is not secured to any wall therein. As previously mentioned, inflation and deflation of the balloon 300 may be difficult due to the mobile nature of the balloon 300. In conventional applications, the balloon 300 is removed from the stomach. With the present check valve 100, attachment 200, and docking station, the balloon 300 is capable of being inflated or deflated while the balloon 300 remains in the patient's stomach. That is, as will be described below, the check valve 100 may be immobilized and aligned with a tool, the tool configured to open the valve and allow flow into or out of the balloon 300 as necessary. The fluid allowed to flow through the check valve 100 may be liquid, air, inflation fluid, or other fluid in accordance with principles of the invention.

Figure 4:
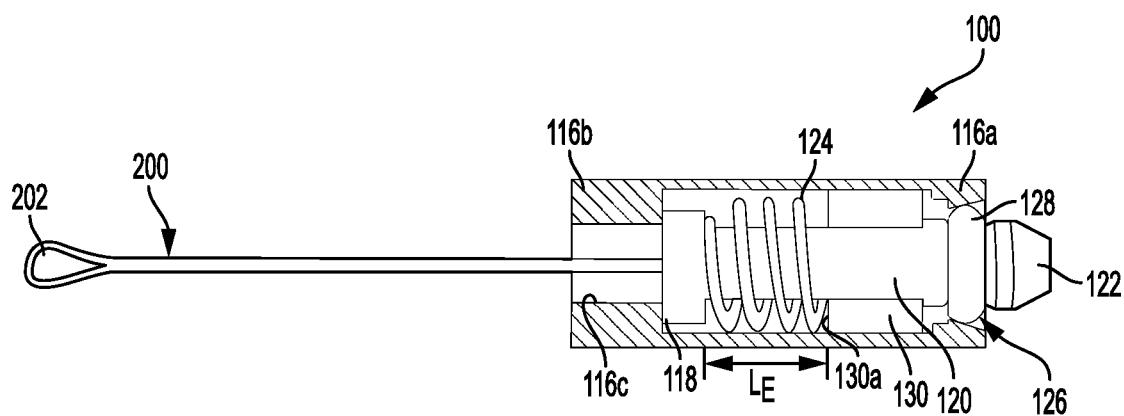
FIG. 4 shows a close-up view of the check valve of FIG. 3, with the valve in the closed position.

FIG. 4 depicts a close-up view of the check valve 100 with the balloon 300 omitted for clarity. The check valve 100 in FIG. 4 is depicted in a closed position. The check valve 100 may be biased in the closed position by a spring 124. In this manner, once inflated or deflated to the appropriate level, the check valve 100 may retain the balloon 300 (not depicted) in the desired state. The check valve 100 may include a housing 116, a plunger head 118, a plunger arm 120, a plunger tail 122, the spring 124, an o-ring 128, and a block 130. The housing 116 may be formed as a single piece or may be formed as a first housing portion 116a and a second housing portion 116b coupled together. The entry 126 may be formed integral with an interior surface of the housing 116 or may be a separate piece secured (e.g. with threads or fasteners) to an interior surface of the housing 116. The block 130 may be built into, integrally formed with, or otherwise secured to the housing 116. Thus, the block 130 may be a stationary, non-moving component against which the spring 124 may be compressed. Alternatively, the block 130 may be permitted to move a small distance until engagement with an interior surface of the housing 116. As may be appreciated, the spring 124 may be compressed between the surface 130a of the block 130 and a distal surface of the plunger head 118.

In the check valve 100, the plunger head 118, plunger arm 120, and plunger tail 122 may all be connected as one unit, similar to the check valve 10 of FIG. 1. Alternatively, the plunger head 118, plunger arm 120, and plunger tail 122 may be formed integrally. The plunger arm 120 may be formed as a solid piece as is the plunger arm 20 of FIG. 1. Alternatively, the plunger arm 120 may be split in the middle, leaving space for other parts, such as the string 200, to be connected to the block 130 within the housing 116 of the check valve 100, as will be described in relation to FIG. 5.

With continued reference to FIG. 4, in the closed position, the spring 124 may be extended to a length LE pushing the plunger head 118 to the left in FIG. 4. In the closed position, the plunger tail 122 may hold the o-ring 128 in a sealing position with the entry 126 to the interior cavity (114 in FIG. 3) of the balloon 300 (FIG. 3). The closed position of FIG. 4 may be the normal position of the check valve 100. That is, the spring 124 may bias check valve 100 to a normally closed position. It may be appreciated that the plunger 118, 120, 122 may slide with respect to the block 130. That is, the block 130 may extend through an interior of the plunger arm 120 (FIG. 5) and the plunger may move with respect to the block 130 to compress the spring 124 against the block 130 and extend the o-ring 128 off of the entry 126 allowing flow therethrough.

Figure 5:
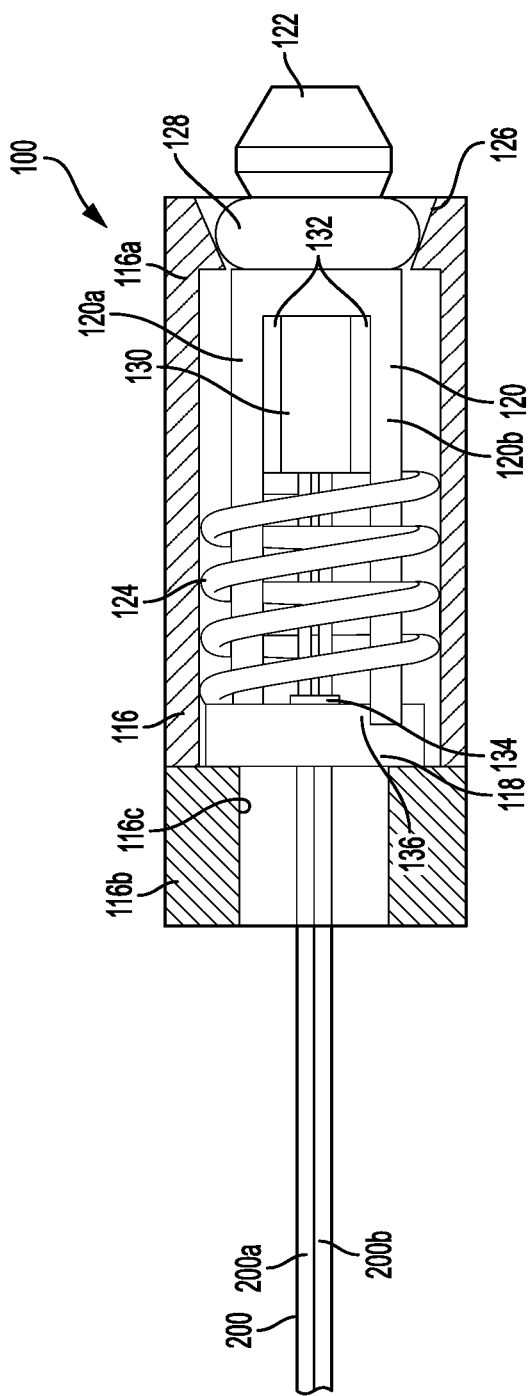
FIG. 5 shows a close-up view of the check valve of FIG. 3 from a perspective rotated 90° relative to the view shown in FIG. 4.

Referring now to FIG. 5, a close-up view of the check valve 100 of FIG. 4 is shown, rotated 90° from the perspective of FIG. 4. The plunger head 118, plunger arm 120, and plunger tail 122 of the check valve 100 may be formed as a single, integral piece or may be formed as separate parts coupled or secured together. The plunger head 118 may be generally cylindrical with a hole (not shown) through which the string 200 may pass. The plunger head 118 may be disc shaped. The hole may be located in the center of the plunger head 118 or may be located anywhere through plunger head 118 to facilitate connection of the string 200 to the block 130. The plunger head 118 may further include a silicone seal 134 for sealing the hole and the string 200 within. The silicone seal may prevent fluid from passing through the hole having the string 200. The plunger head 118 may include a cut out or groove 136 for coupling to the plunger arm 120. Alternatively, the plunger head 118 and the plunger arm 120 may formed as an integral piece.

With continued reference to FIG. 5, the plunger arm 120 may be cylindrical. The plunger arm 120 may be split in the middle such that a cavity 132 is located between opposing sides 120a and 120b of the plunger arm 120. At the proximal end, the plunger arm sides 120a, 120b may be coupled or integral with the plunger head 118. At the distal end, the plunger arm 120 main (cylindrical) body may be coupled to or integral with a neck (not shown) that is in turn coupled or integral with the plunger tail 122. The neck may have a reduced diameter from the plunger arm 120 and/or plunger tail 122 such that the o-ring 128 may be fitted around the neck. The string 200 may have two ends 200a, 200b which extend through the plunger head 118 and through the cavity 132 of the plunger arm 120. The two ends 200a and 200b may then be coupled, secured, or attached to the block 130. Alternatively, the string 200 may be one or multiple strings with knots, loops, or components that may allow for grasping by a tool. As previously described, the plunger, including plunger arm 120, may be allowed to move with respect to the block 130 and the housing 116.

Figure 6:
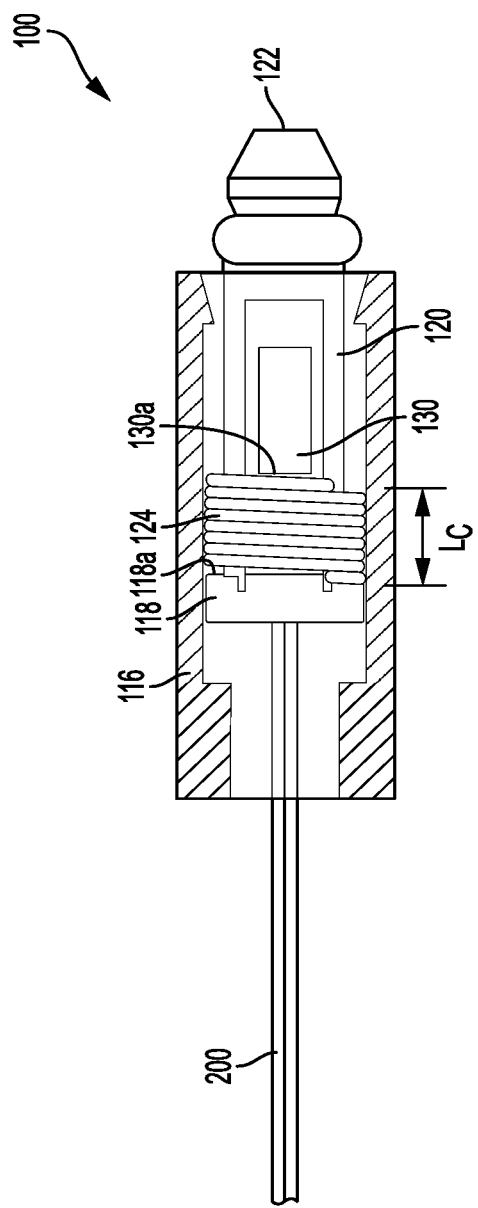
FIG. 6 shows a close-up of the check valve of FIG. 3 in an open position according to an embodiment of the present invention.

Referring now to FIG. 6, the check valve 100 is depicted in an open position, with the balloon 300 (FIG. 3) removed for clarity. In the open position, the plunger head 118 may be pushed to the right in FIG. 6 within the housing 116. Pushing or moving the plunger head 118 may shorten the spring 124 to the contracted length $L_e$. As may be appreciated, the spring 124 may be secured between a proximal surface 118a of the plunger head 118 and a distal surface 130a of the block 130. In this manner, the block 130 may operate as a stopper beyond which the spring 124 cannot pass. As the plunger head 118 is moved or pushed to the right, plunger arms 120 are correspondingly moved or pushed to the right due to the integral or coupled nature of the components. The plunger arms 120 move the neck (not depicted) and plunger tail 122 into the interior cavity 114 (FIG. 3) of the balloon and out of the housing 116. As the plunger tail 122 is moved out of the housing 116, the o-ring 128 is moved away from the entry 126, thus unseating the o-ring 128 from the entry 126 and allowing flow into and out of the interior cavity 114 of the balloon 300.

Figure 7:
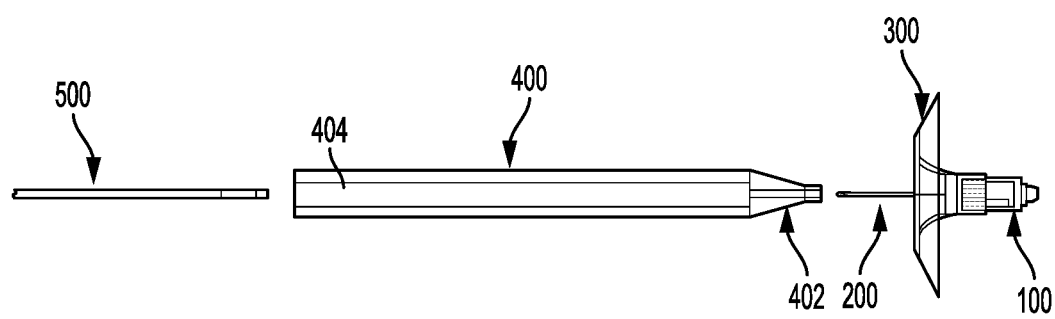
FIG. 7 shows a catheter to be used in conjunction with the balloon and check valve and a step in a method of operating the check valve of FIG. 3, according to an embodiment of the present invention.

FIG. 7 shows an embodiment of an impacting member as a catheter 400, which may, for example, have a 2-3.5 mm outer diameter with a wall thickness of 0.1 to 0.6 mm. The catheter 400 may be made of a semi-flexible material that allows the catheter to assume curves up to 90 degrees, yet at the same time maintain rigidity. Materials such as Teflon, low friction synthetic polymers, polymers coated with materials that produce a non-friction surface such as parylene or Teflon, and other material types may be employed. The catheter 400 may have a lumen with a diameter of 0.8 to 3.3 mm. The catheter 400 may be used in conjunction with the check valve 100. The catheter 400 may be made of any suitable biocompatible material or material used for medical devices. The catheter 400 may have a tip 402, but is not limited to the shape shown in FIG. 7. The tip 402 may be tapered, a luer, cone shaped, straight, or rounded tip. The tip 402 may facilitate entry of the catheter 400 into an opening 116c of the housing portion 116b. The opening 116c may be a proximal opening of the housing 116 and the entry 126 may be a distal opening of the housing 116. The catheter 400 may have a central lumen 404 through which a grasping tool 500 may extend. The grasping tool 500 may grab or secure the easy grasp loop 202 (FIG. 3) of the string 200, as will be described to follow. The tip 402 may encounter the plunger head 118 during operation of the check valve 100 to move the plunger head 118 and thus open the check valve 100. As may be appreciated, the proximal end 116b, opening 116c, the plunger head 118, and the string 200 may be considered a docking station for the check valve 100. That is, the catheter 400 is aligned with and impacted with these components such that alignment and operation of the check valve 100 are permitted. In this regard, the components act as a docking station for the catheter 400 and tool 500.

Figure 8:
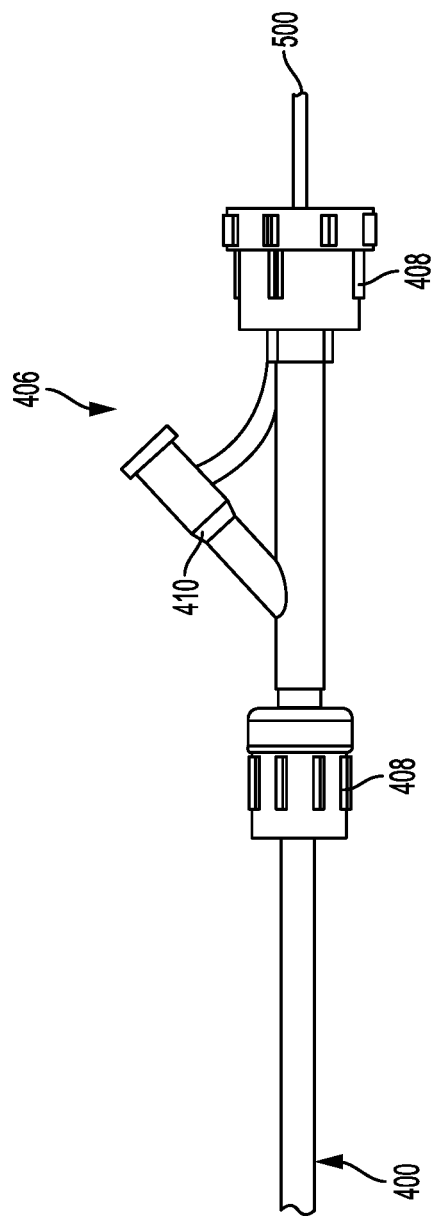
FIG. 8 shows a portion of the catheter, according to an embodiment of the present invention.

Referring to FIG. 8, a proximal part 406 of the catheter 400 may be Y-shaped with a homeostatic valve 408 at each arm that may be tightened or loosened to regulate flow and thereby prevent backflow outside of the catheter 400. The proximal part 406 may include an inflation and/or deflation site 410 for inflating and/or deflating the balloon 300. The proximal part 406 may have a handle with mechanical control that closes and opens the hook 502 (FIG. 10) of grasping tool 500, or a handle that closes and opens the grasper of any type of grasping device.

Figure 9:
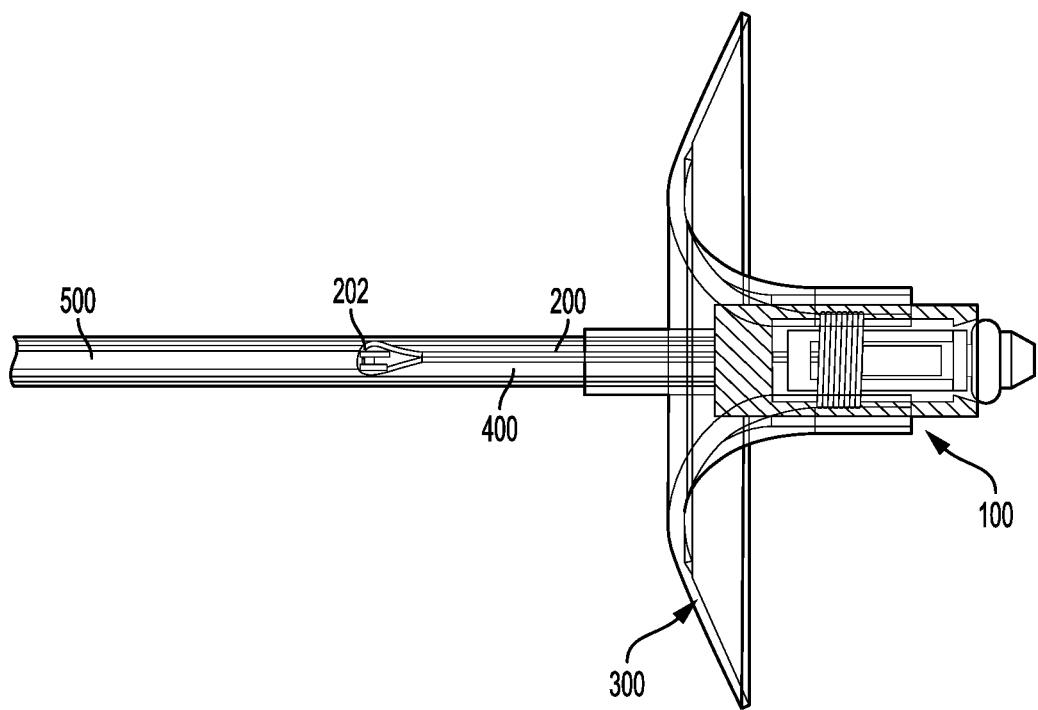
FIG. 9 shows a check valve in operation with a catheter and a grasping tool, according to an embodiment of the present invention.

Referring to FIG. 9, during operation, an endoscope is extended into a patient's stomach. A catheter 400 with a grasping tool 500 are inserted therethrough. The grasping tool 500, such as grasping forceps used in endoscopic procedures may be inserted into the lumen 404 of the catheter 400 through the homeostatic valve 408 (FIG. 8). During the procedure, the balloon, check valve, catheter, and grasping tool may all be located within the patient's stomach. The forceps or similar grasping tool 500 may grasp the string 200 by the easy grasp loop 202 and pull the check valve 100 toward the catheter 400. At the same time, the catheter 400 may be advanced toward the check valve 100. This may easily guide the grasping tool 500 to the target, the opening 116c, of the check valve 100. The catheter 400 then enters the opening 116c of the housing 116 of the check valve 100. Such alignment of the catheter 400 with the check valve 100 allows for immobilization of the check valve 100.

While fixating the catheter 400 and gastroscope with one hand, the grasping tool 500 (now grasping string 200) within the catheter 400 is pulled back with the other hand. This motion causes the tip 402 to releasably engage the plunger head 118 of the check valve 100. Continued pulling of the string 200 pushes the catheter tip 402 into releasably impacting the housing 116 and thereby causing the plunger head 118 to move to the right (as shown in the figures) or towards the interior cavity 114 of the balloon 300. This movement causes the plunger arm 120 and the plunger tail 122 to move to the right which thereby unseats the o-ring 128 and opens the check valve 100. At the same time, the tip 402 of the catheter 400 impacts into the housing 116. Alternatively, the catheter 400 may be straight, and the opening 116c of the housing may be cone shaped resulting in the same impaction effect. The catheter 400 may impact into the housing 116, which maintains the check valve 100 in an open position. The distal movement of the plunger head 118, the plunger arm 120, and the plunger tail 122, the check valve 100 opens to bi-directional flow by separating the o-ring 128 from contacting the entry 126. Once the catheter 400 is impacted and the check valve 100 is open, the string 200 may be released by the grasping tool 500 and the grasping tool 500 may be pulled out of the catheter 400. This may open more space in the lumen 404 and allow enhanced flow of fluid. Alternatively, the grasping tool 500 may be left in place and flow may continue at a slower pace.

After inflation or deflation is completed, the catheter 400 may be removed from the docking station or entry to the check valve 100. The tool 500, catheter 400, and endoscope may be removed from the patient's stomach and from the patient.

The force of the catheter 400 on the check valve 100 to impact and disengage the check valve 100 may be between 0.8 kg and 2 kg. The forces to contract and relax the spring 124 may be less than the forces that impact the valve by 25% to 40%. If the spring forces are greater than the impaction forces then the spring 124 may disengage the catheter 400 from the check valve. 100

With continued reference to FIGS. 3-9, and described in another manner, during operation, the grasping tool 500 exits the endoscope and grasps the easy grasp loop 202 of the string 200. The grasping tool 500 may be pulled while the tip 402 of the catheter 400 has entered into the check valve 100 of the balloon 300. The catheter 400 may enter with ease, until the tip 402 broadens and impacts the plunger head 118 inside the housing 116 of the check valve 100. The grasping tool 500 may be pulled hard to impact the catheter 400 into the check valve 100. If the catheter 400 is not impacted into the check valve 100, the check valve 100 may close prematurely. As the catheter 400 impacts inside the housing 116, the catheter 400 pushes the plunger head 118 toward the entry 126 (compressing the spring 124). This in turn pushes the plunger arm 120 and the plunger tail 122 forward, unseating the o-ring 128 from the entry 126, and opens the check valve 100 to bi-directional flow. At this point the grasping tool 500 may release the string 200 (since the cone-tipped catheter 400 is impacted inside the housing 116). The grasping tool 500 may then be pulled out of the catheter 400. At this time, fluid may be admitted from the inflation site 410 (or removed through the deflation site 410), though the lumen 404 of the catheter 400, through the entry 126 of the check valve 100 and into the interior cavity 114 of the balloon 300. With reference to FIG. 6, the flow may enter the opening 116c of the housing 116, flow around the plunger head 118, around and through the plunger arms 120, through the entry 126, and past the o-ring 128 and plunger tail 122. It may be appreciated that during deflation, flow may follow the same path in the reverse direction. Once inflation/deflation is completed, the catheter 400 is pulled out of the check valve 100 and the spring 124 expands to its preferred position, which brings the plunger head 118, plunger arm 120, and plunger tail 122 back to the closed position (FIG. 5) with the o-ring 128 sealed in the entry 126 and flow of fluid prevented.

Although the catheter 400 is described as impacting the check valve 100, the catheter may be forced into the valve in other manners. For example, the catheter 400 may be secured to the check valve opening 116c with a turning motion. That is, the catheter 400 may have a tip 402 which may be screwed or threaded into the valve opening 116c. One may appreciate that the inner surface of opening 116c and the outer surface of the catheter tip 402 may have complementary threads or other surfaces to allow the rotational and longitudinal movement.

Figure 10A:
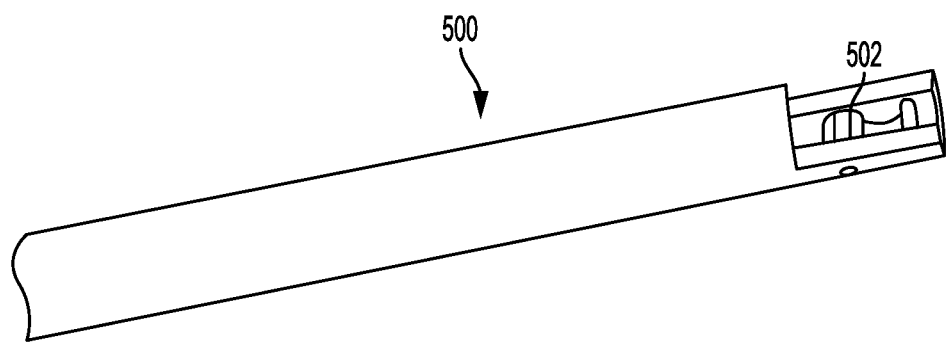
FIG. 10A shows an exemplary grasping tool in a closed position, according to an embodiment of the present invention.
Figure 10B:
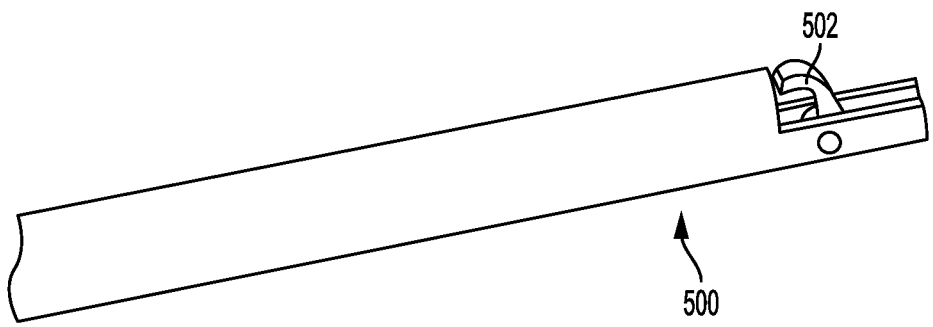
FIG. 10B shows an exemplary grasping tool in an open position, according to an embodiment of the present invention.
Figure 11:
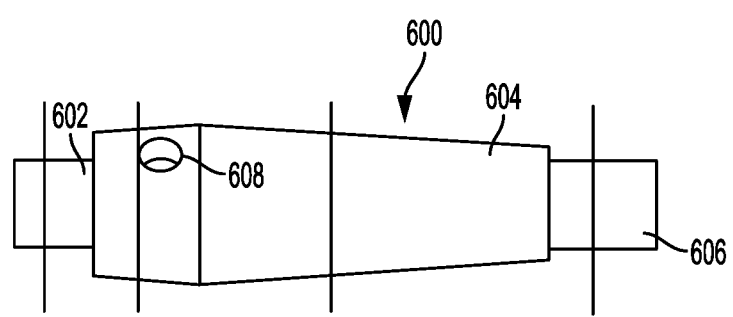
FIG. 11 shows a biluminal connector, according to an embodiment of the present invention.

FIGS. 10A and 10B depict the grasping tool 500 in an open (FIG. 10A) and closed (FIG. 10B) position. In the open position, the grasping tool 500 may have a hinged arm or hook 502 (or other connection type) that may align with the easy grasp loop 202 (FIG. 3) of the string 200. Once properly aligned, the hinged arm or hook 502 may be actuated to close thus enclosing the easy grasp loop 202 and securing the grasping tool 500 to the check valve 100 via the string 200. Once grasped, the grasping tool 500 may be pulled to pull the string 200 and thus the check valve 100 and balloon 300 into alignment with the catheter 400. After proper alignment, the aforementioned impacting and opening of the check valve 100 may be performed. The grasping tool 500 may then be opened to release the check valve 100 (after impaction and/or opening). The grasping tool 500 may have a curved end that is hinged and can be opened to a straight position. In the closed position (FIG. 10B), the length of the hinged arm or hook 502 is within 0.5 to 2 mm of the inner diameter of the catheter. The hinged arm or hook 502 may be moved into a position that can grasp (FIG. 10A) or to a position that does not grasp (FIG. 10B). The grasping tool 500 may alternatively be other types of grasping tools, such as a rat-tooth grasper or hook grasper.

Thus, as may be appreciated from the foregoing disclosure, during a procedure to inflate and/or deflate the balloon, a catheter may be inserted into the channel of a standard flexible gastroscope, as practiced routinely by those skilled in the art of gastrointestinal endoscopy. As previously mentioned, the check valve and method of aligning and opening the check valve may be utilized in other body cavities or for industrial, plumbing, pipelines, wellbores, or other non-medical uses. For example, a check valve may be located in a pipeline. The pipeline may be inaccessible from the outer surface (e.g. a buried pipeline). The check valve may be biased to a normally closed position (as previously described) or biased to a normally open position. When it is desired to open or close the check valve, a grasping tool, similar to the grasping tool 500 but sized and dimensioned to fit in a pipeline instead of a catheter, may be extended into the pipeline inside another device (e.g. inside a tubular snake). Once inside the pipeline, the grasping tool may grasp a loop on a string coupled to the pipeline and align an impacting device (similar to the impacting catheter 400) with an opening of the check valve. The grasping tool may pull the impacting device into alignment and impact the check valve in a manner similar to that previously described to effectuate opening and/or closing of the check valve.

In an alternative embodiment shown in FIGS. 11-14, the flow of inflation/deflation fluid may be separated from the lumen having the grasping tool 500. There may be a need to separate the grasping tool 500 from the flow of inflation fluid for fear of gastric fluid contamination. This may be accomplished using a biluminal connector 600. In this embodiment, the catheter 400 may be replaced with the biluminal connector 600 having a proximal end 602 which sits in a distal end of a channel of a gastroscope 800 (FIG. 13). The biluminal connector 600 may have a distal end 604 which impacts the check valve 100 (not depicted). The distal end 604 may have a tip 606 for guiding the tool into alignment into the check valve 100. The tip 606 may be the same as or similar to the tip 402 of the catheter 400. The biluminal connector 600 may further have an opening 608 in the side wall of the biluminal connector 600. The opening 608 may allow entry and/or exiting of the inflation and/or deflation fluid.

The immobilization of the balloon with the grasping of the string can be performed with the grasping tool, as previously described. The grasping tool may be alone in the gastroscope channel and the inflation may be performed in a second channel, separated from the gastroscope channel.

Figure 14A:
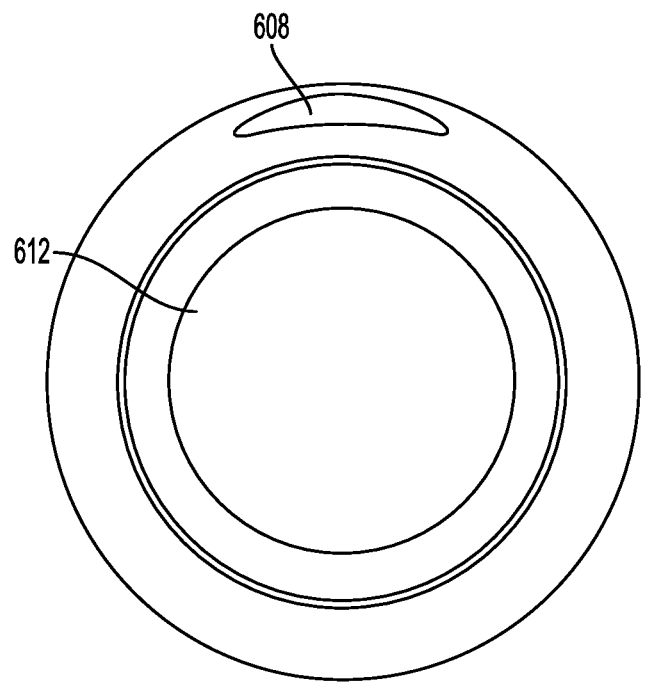
FIGS. 14A-14E show cross-sectional views of the biluminal connector of FIG. 11 taken along various axes of FIG. 11, according to an embodiment of the present disclosure.
Figure 14B:
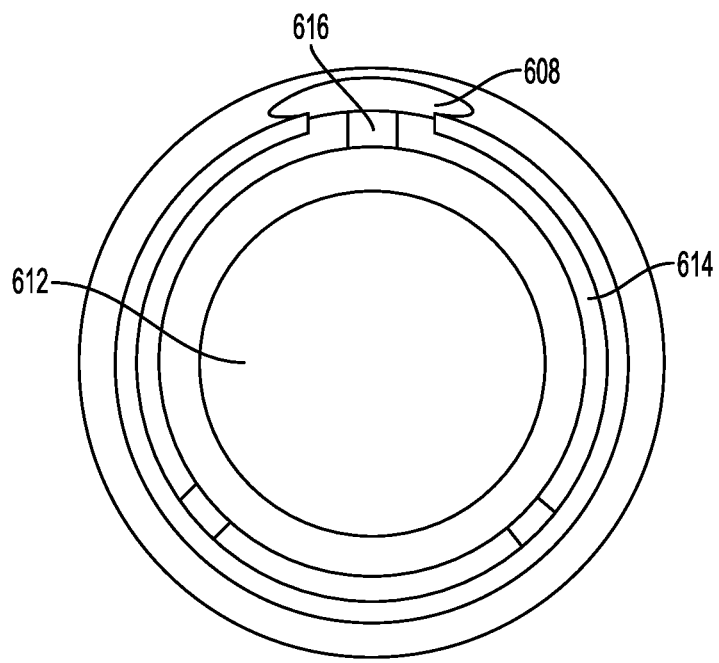
Figure 14C:
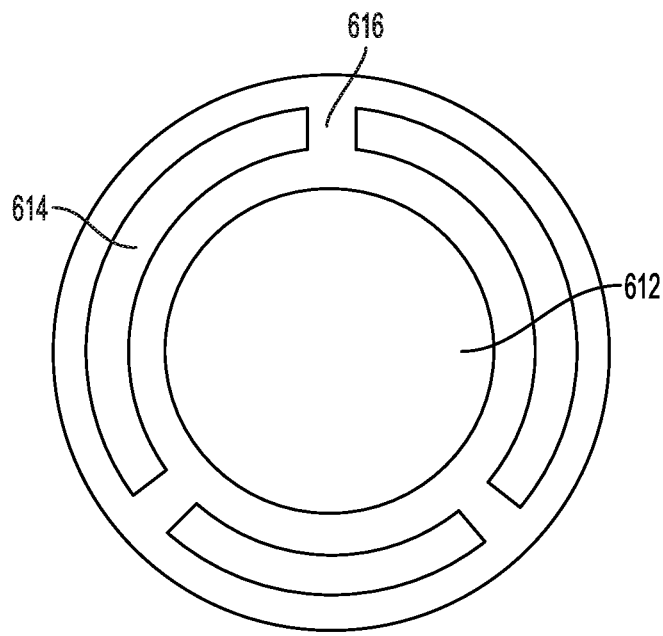
Figure 14D:
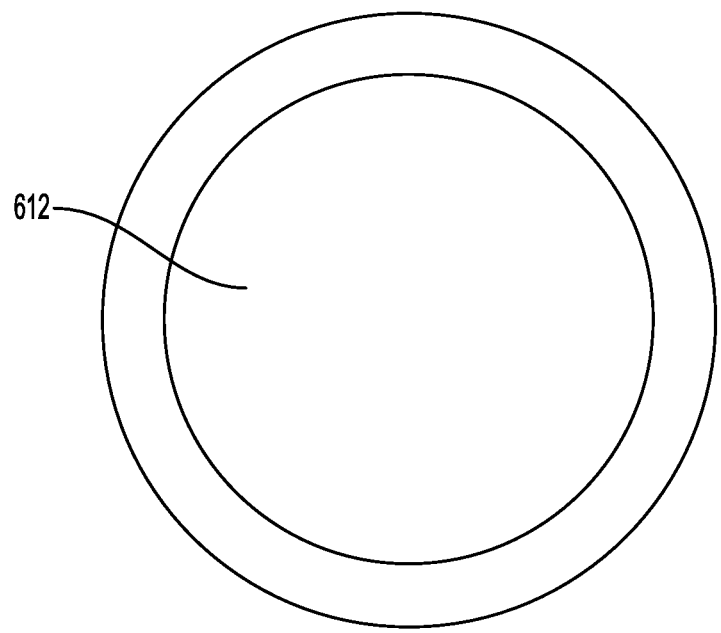

The biluminal connector 600 may have two lumens, as best depicted in FIGS. 14B and 14C. A first, central lumen 612 may extend from the proximal end 602 (see FIG. 14A) to the distal end 604 (see FIG. 14E). Once coupled to the gastroscope, the first lumen 612 may allow entry of the grasping tool 500 through the gastroscope channel and through the first lumen 612 to allow for grasping, alignment, and impaction of the check valve 100 as previously described. The first lumen 612 may be wholly separated from a second lumen 614 (FIGS. 14B, 14C). The second lumen 614 may be an annular lumen extending circumferentially around the outer surface of the first lumen 612 such that the first lumen 612 and the second lumen 614 are concentric. The second lumen 614 may be located distally to the gastroscope 800. The second lumen 614 may be open distal to the gastroscope channel and allow entry from an outer side channel parallel to the gastroscope 800. The entry may be located through opening 608 such that a flexible tube may be coupled to opening 608 to allow for bi-directional flow (inflation and/or deflation) through the flexible tube, second lumen 614, and check valve 100 (not depicted). The external channel provided in the flexible tube may run parallel to the gastroscope 800 and then may turn in to the distal end of the gastroscope 800 and enter the second lumen of the biluminal connector 600.

Figure 12:
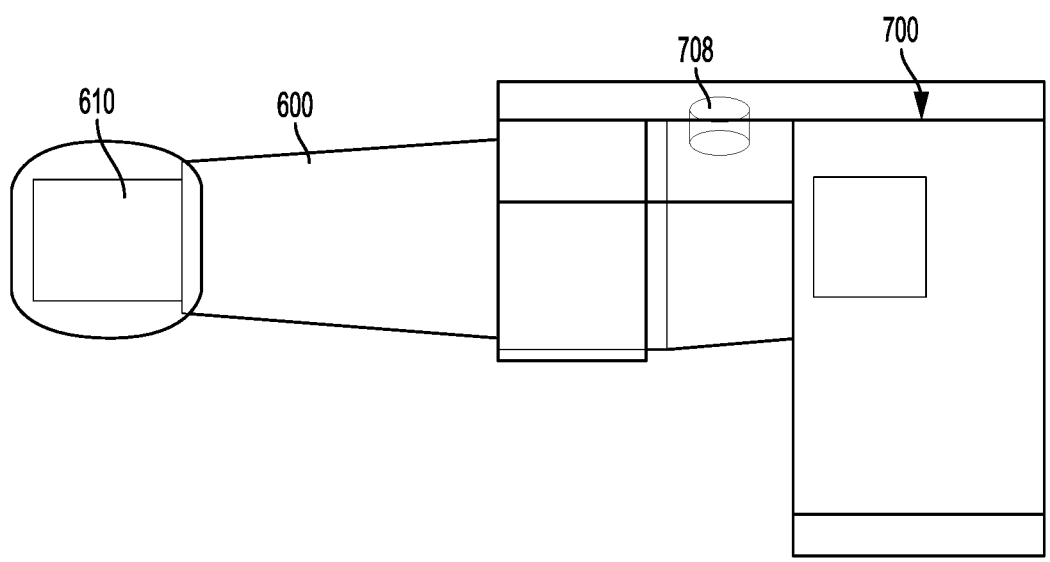
FIG. 12 shows the biluminal connector of FIG. 11 with a coupling sleeve, according to an embodiment of the present disclosure.

Referring to FIG. 12, the biluminal connector 600 may have a silicone sleeve 700 to secure the biluminal connector 600 to the gastroscope 800. The sleeve 700 may have an opening 708 which aligns with the opening 608 of the biluminal connector 600. The biluminal connector 600 may be stabilized on the distal end of the gastroscope 800 (FIG. 13) with the sleeve 700. The biluminal connector 600 may further have a plug 610. The plug 610 may have a rounded or atraumatic distal tip that may be placed into the distal opening of the biluminal connector 600. The plug 610 may be pushed out by the grasping tool at any time. The plug 610 may be silicone or other flexible rubbery material or can be made of a material that melts at body temperature such as those used with medication capsules.

Referring to FIG. 13, the sleeve 700 may fit snugly around the distal end of the gastroscope 800. The inflation tube may be external to the gastroscope and enter through the opening 708. The biluminal connector 600 may have the proximal end 602 sitting within the distal channel of the gastroscope 800. The distal tip 606 may enter the check valve 100 (FIG. 3) and move the plunger head, the plunger arm, and the plunger tail distally. Near the distal end of the biluminal connector 600, the body widens with its tapering profile to impact within the check valve 100. As may be appreciated, the biluminal connector may prevent contamination of inflation fluid with gastric fluid and may allow the gastroscope channel to utilize its suctioning function during the procedure.

Figure 14E:
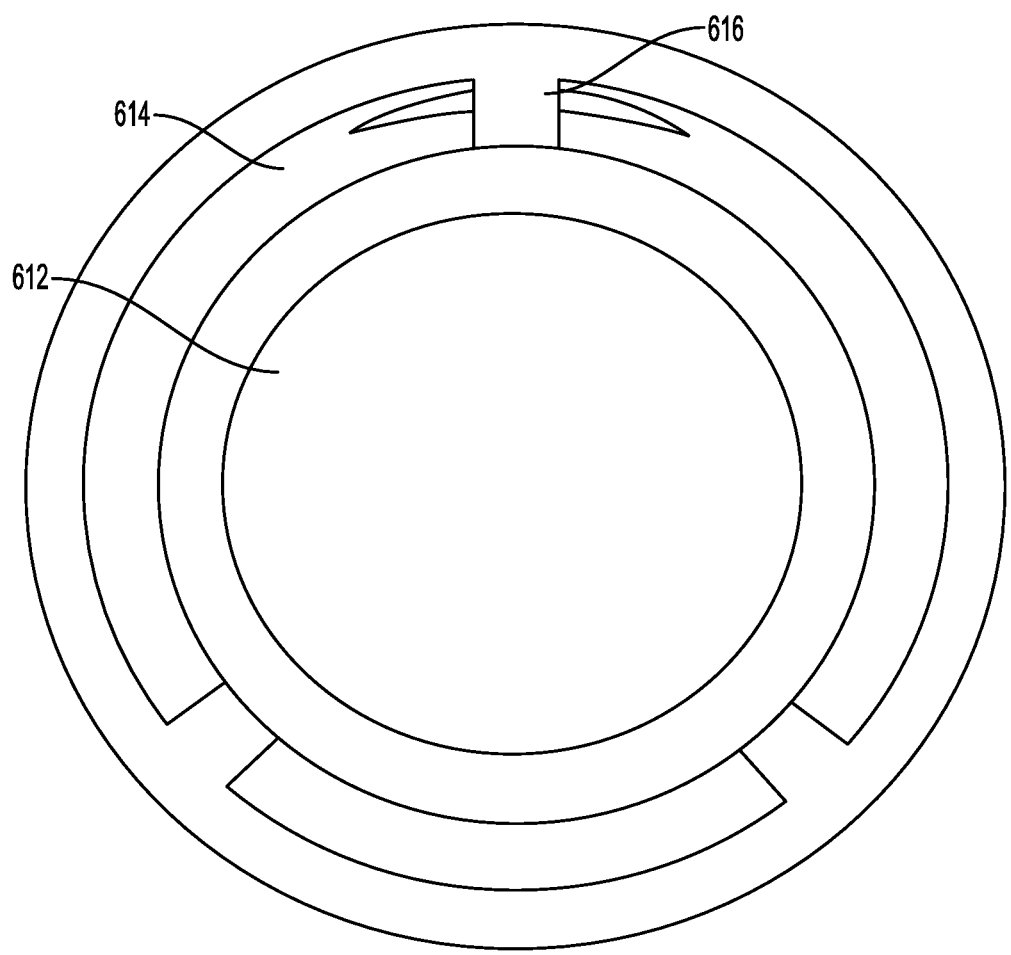

FIGS. 14A-14D depict cross-sectional views of the biluminal connector 600 taken along the lines A, B, C, and D of FIG. 1. FIG. 14E depicts a cross-sectional vie of the biluminal connector 600 at the distal end. FIG. 14A shows the first lumen 612 which sits within the gastroscope channel and allows entry of the grasping tool. FIG. 14B shows the opening 608 through which the external inflation channel enters into the second lumen 614 which is an outer concentric lumen to the first lumen 612. FIG. 14C shows the concentric bilumena with supporting walls 616. FIG. 14B shows the first lumen 612 through which the tool travels and grasps the string 200 (FIG. 3).

The biluminal connector 600 may be made from silicone or a firmer material, such as Teflon or other synthetic material. The biluminal connector 600 may have a wall thickness of 0.2 to 5 mm with a central lumen of 0.8 to 2.20 mm that accommodates a grasping tool with an external diameter of 0.7 to 3.0 mm. The biluminal connector 600 may be 6-15 mm long and 3-12 mm wide.

Figure 15:
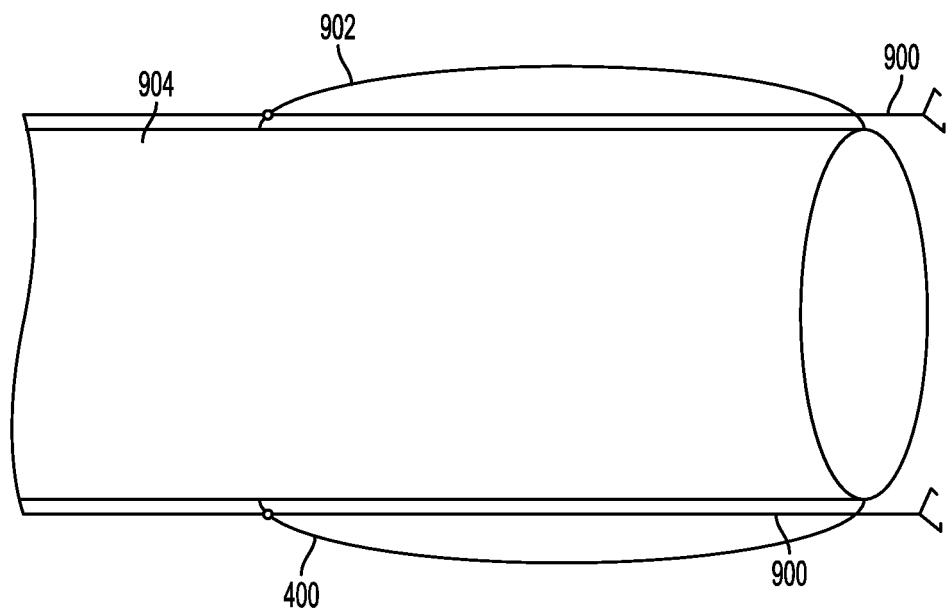
FIG. 15 shows an alternative method for grasping the string, according to an embodiment of the present disclosure.
Figure 16:
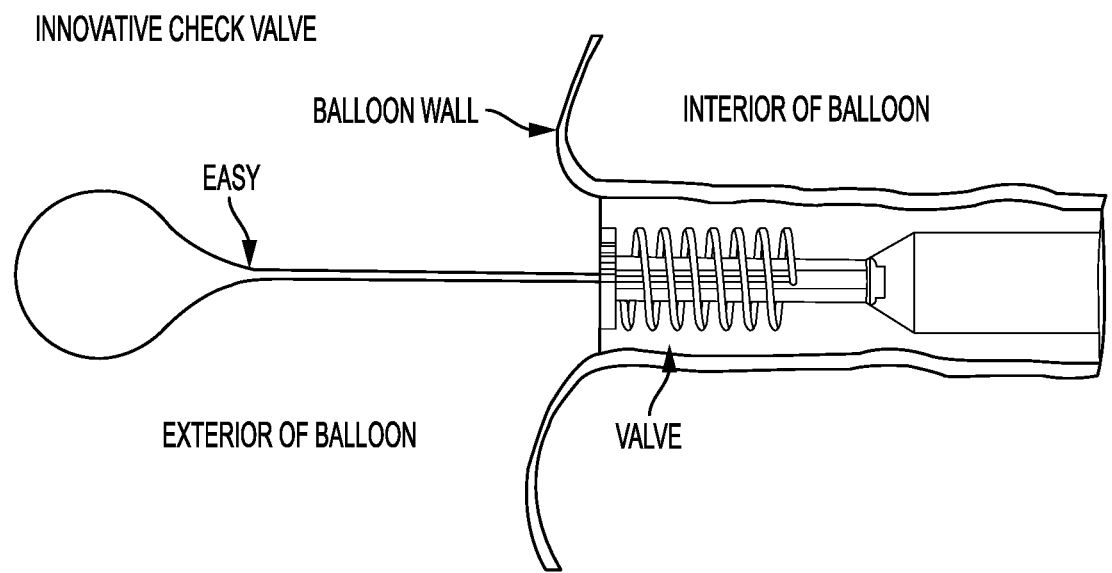
FIG. 16 shows a check valve in a gastrointestinal balloon according to another embodiment of the present invention.
Figure 17:
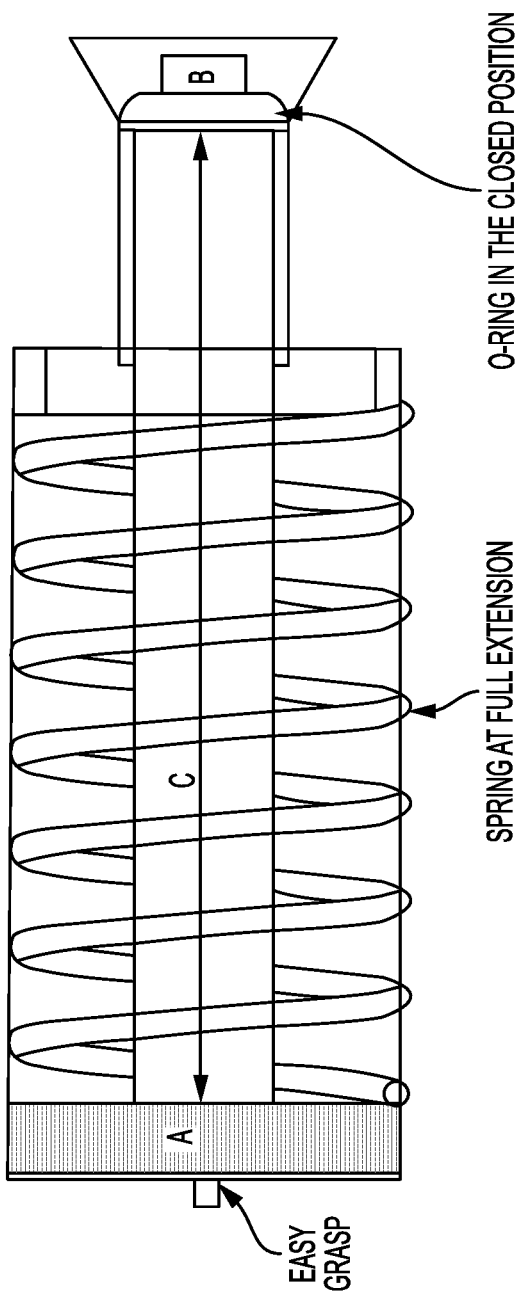
FIG. 17 shows a close-up view of the check valve of FIG. 16, with the valve in the closed position.
Figure 18:
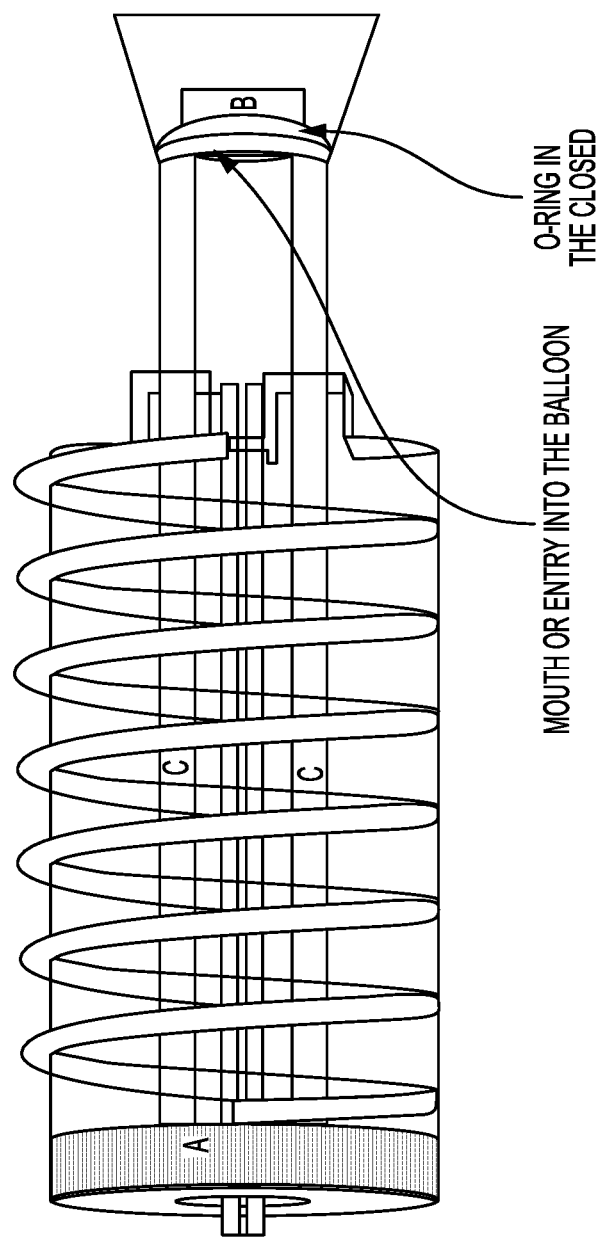
FIG. 18 shows a close-up view of the check valve of FIG. 16 from a perspective rotated 90° relative to the view shown in FIG. 17.
Figure 19:
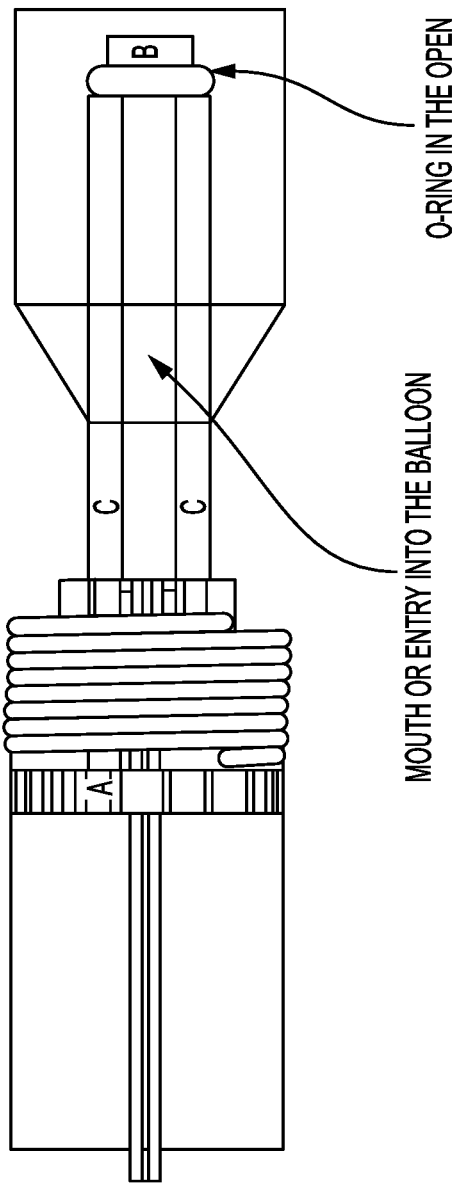
FIG. 19 shows a close-up of the check valve of FIG. 16 in an open position according to an embodiment of the present invention.
Figure 20:
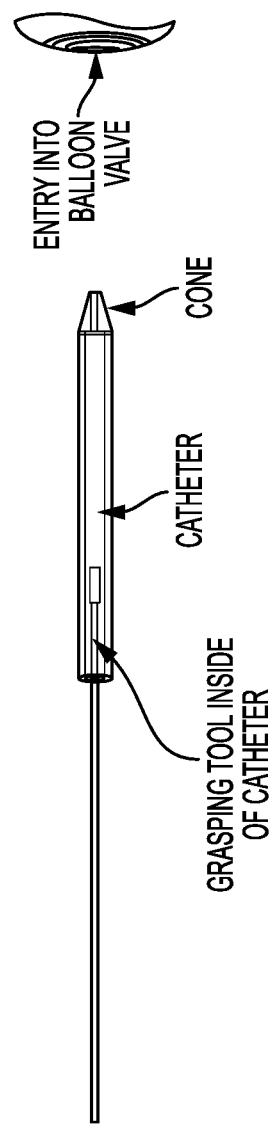
FIG. 20 shows a catheter to be used in conjunction with the balloon and check valve of FIG. 16 and a step in a method of operating the check valve, according to an embodiment of the present invention.
Figure 21:
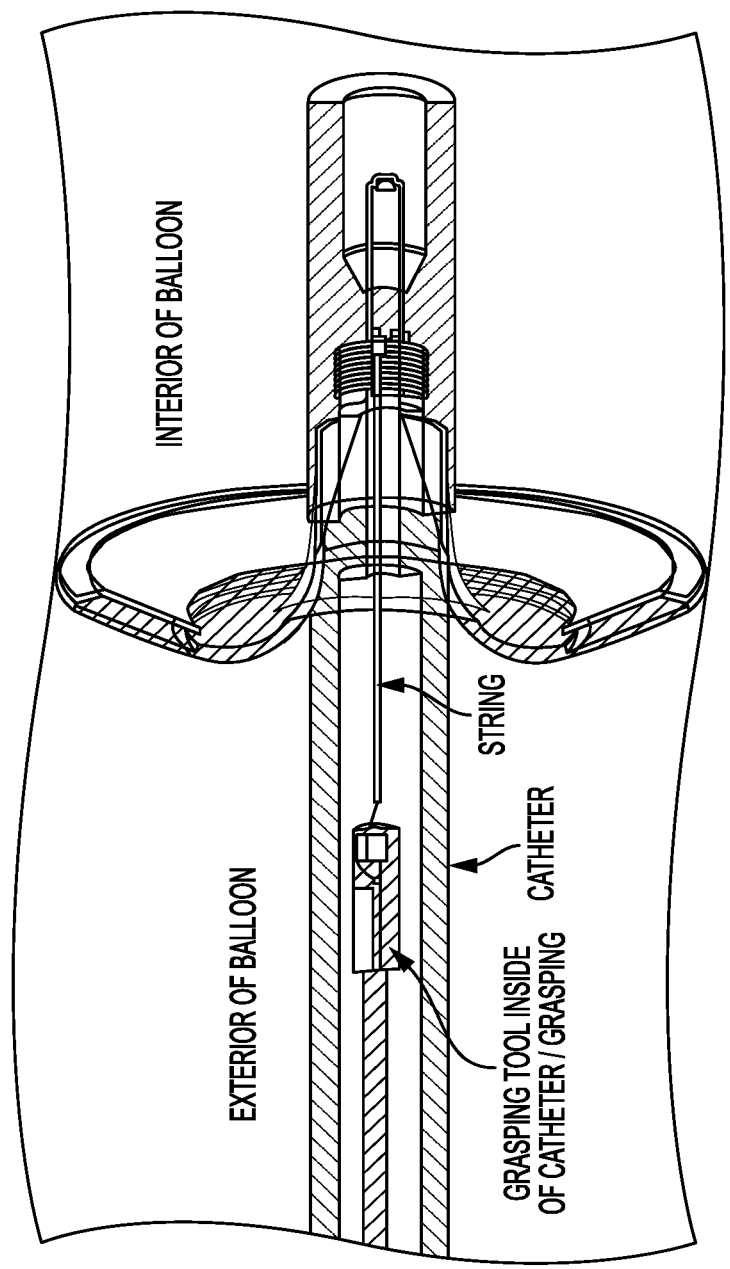
FIG. 21 shows a check valve in operation with a catheter and a grasping tool, according to an embodiment of the present invention.

Referring to FIG. 15, an alternative approach to accessing the balloon valve within the stomach is to separate the immobilization of the balloon from the accession of the valve. One method of immobilization is to place handles on the balloon (not depicted) that are grasped by the scope. Following this immobilization step, the valve (check valve, duck valve, or any type of valve) is accessed with a catheter that enters from the lumen of the endoscope into the valve and opens the valve, as previously described. Upon withdrawal of the catheter the valve closes. Following closure of the valve, the immobilization of the balloon is discontinued. As an example of the handles on the balloon one could place two loops of string (nylon for example) at the 3 o'clock and 9 o'clock positions of the valve housing. The two loops may be grasped by two grasping forceps 900 that exit at the 3 o'clock and 9 o'clock positions in a sleeve 902 that surrounds the endoscope 904. The two forceps 900 grasp the two loops (not depicted) and pull them toward the endoscope tip and immobilize the balloon. The sleeve 902 may be a silicone sleeve with a lumen for one or more grasping forceps 900.

FIGS. 17-21 depict a check valve assembly similar to the check valve 100. As may be appreciated, the exact dimensions and relationships of the valve and plunger may be altered to achieve optimized alignment, immobilization, and actuation of the check valve. For example, as depicted in the embodiment of FIGS. 17-21, the spring may have more or fewer coils. The easy grasp loop of the string may be larger or smaller than depicted in FIG. 3. The string may be formed from multiple strings tied or fastened together. The balloon wall may have a longer stem or a differently contoured outer wall. Other modifications to the balloon, check valve, and catheter are within the scope of this disclosure.

Figure 22:
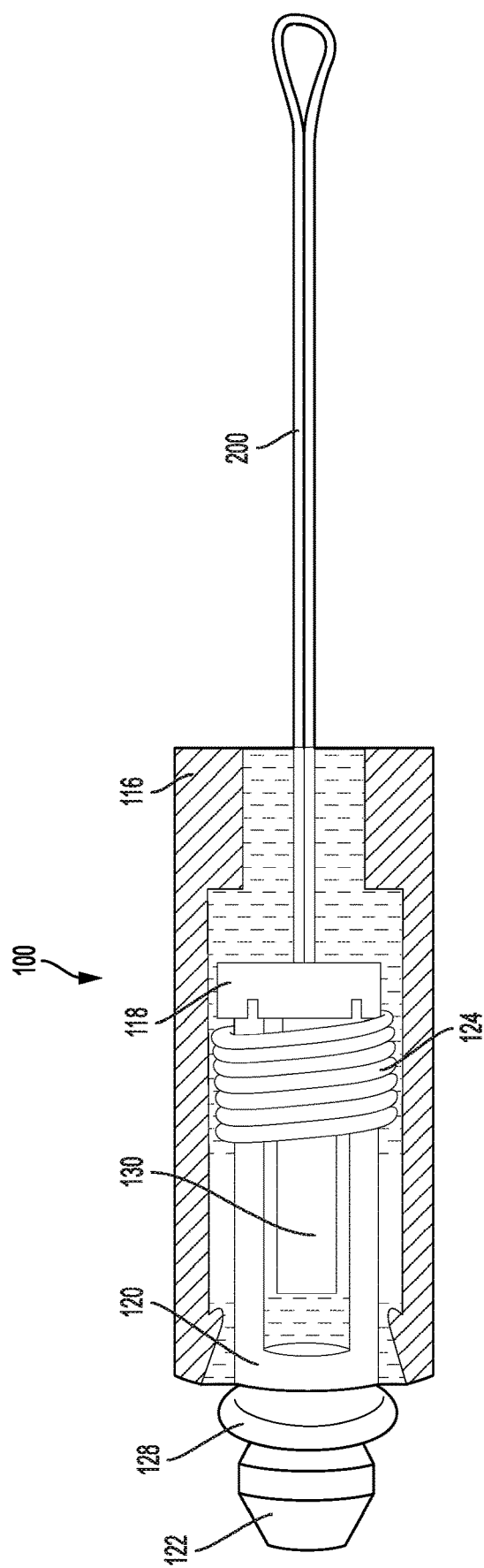
FIG. 22 shows a check valve in an open position with fluid flowing therethrough, according to an embodiment of the present invention.
Figure 23:
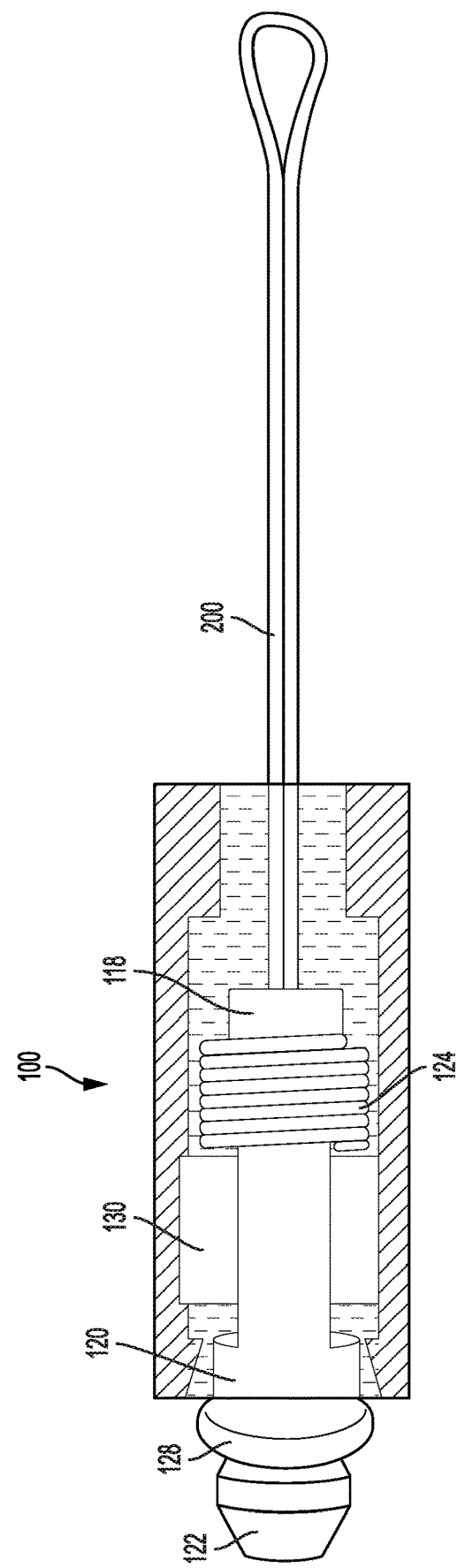
FIG. 23 shows the check valve of FIG. 22 in the open position, rotated 90 degrees from the view of FIG. 22, according to an embodiment of the present invention.
Figure 24:
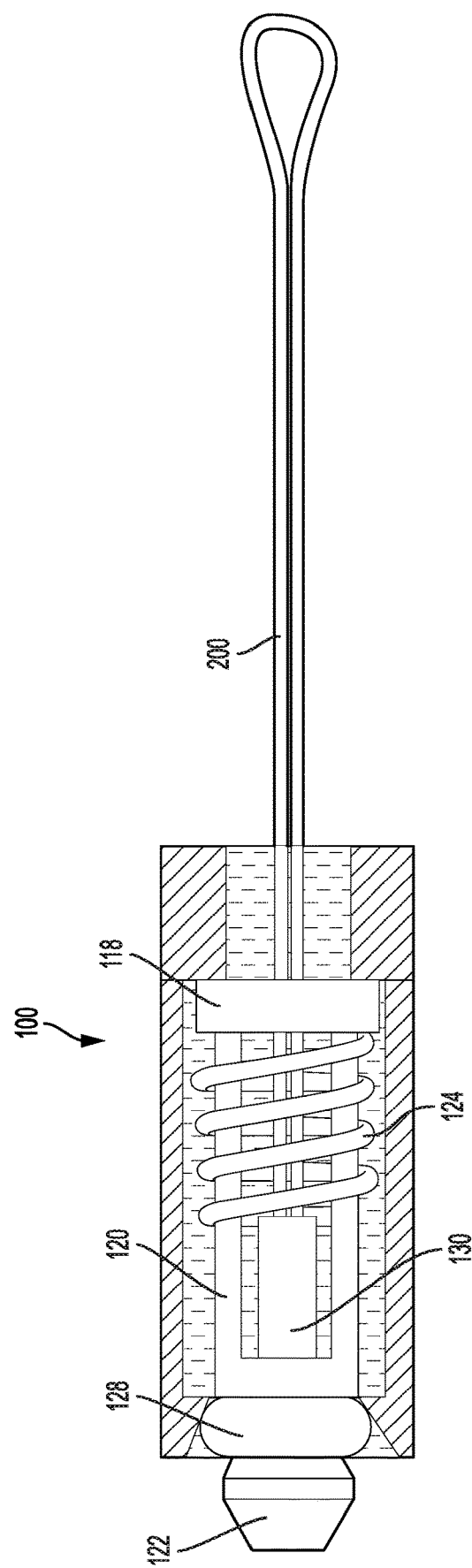
FIG. 24 shows the check valve of FIG. 22 in the closed position, with fluid isolated on either side of the valve, according to an embodiment of the invention.

Referring to FIGS. 22-24, operation of the check valve 100 or check valve of FIGS. 17-21 may be appreciated. For clarity, the catheter 400 is omitted from FIGS. 22-24, but one may appreciate that the catheter 400 would be aligned with the opening to impact the check valve to effectuate opening of the check valve. In the open position of FIG. 22, the plunger including plunger head 118, plunger arm 120, and plunger tail 122 may be seen extending out of the housing 116. In this position, the o-ring 128 is not seated in the opening of the housing 116. The force of the catheter (not depicted) has moved the plunger (including plunger head 118, plunger arm 120, and plunger head 122) toward the interior of the balloon, compressing the spring 124 between the plunger head 118 and the block 130, and moving the o-ring 128 off of the seat of the opening into housing 116. Thus, fluid is allowed to flow between the interior of the valve and the interior of the balloon. The fluid may be seen to flow around the string 200, around the plunger head 118, plunger arm 120, and plunger tail 122, and through the valve opening past the o-ring 128. It may be appreciated that during inflation, fluid may be introduced into the housing 116 through the endoscope and through catheter (not depicted) to inflate the balloon. During deflation, fluid may be removed in the reverse direction to remove fluid from the interior of the balloon.

With reference to FIG. 23, the check valve 100 is still in the open position, but is depicted rotated 90 degrees from the position of FIG. 22. Fluid flow in FIG. 23 flows around the spring 124, plunger 118, 120, 122, and through the distal end opening of the check valve 100. Referring now to FIG. 24, the check valve 100 is depicted in the closed position. As may be appreciated, fluid may be located on the left side of the o-ring 128 (inside the balloon) and on the right side of the o-ring 128 (in the valve housing and in the stomach), however flow between these two areas is not permitted. The spring 124 is shown in the normally extended position, forcing the plunger head 118 toward the right and thus maintaining the o-ring 128 in the closed position.

As may be appreciated from the foregoing disclosure, the check valve of the disclosure may be used in a gastrointestinal balloon. The disclosure further includes a device, system, and method to immobilize the balloon within the body while at the same time providing access to the valve in such a way that the volume can be adjusted. The system can include the balloon and check valve, the catheter, and tool that is configured for grasping onto part of the valve to hold it in place. The disclosure may also include the method of performing this maneuver.

Additionally, the valve may be a check valve, although other valve types (e.g. ball valves, sleeve valves, etc.) may be provided. The check valve may include a spring inside that maintains the valve in a closed position and the spring is compressed to open the valve.

The check valve and balloon may be suitability immobilized while a force is applied to compress the spring. The balloon may be used in the stomach, but may be used for any inflatable, implanted device. The check valve may include a portion that may be grasped by a tool inserted to inflate/deflate the balloon. In some embodiments, this is a loop that extends out from the valve and is grasped by a grasping tool. The loop may be pulled (away from the balloon) by the catheter/device to immobilize the balloon. Grasping forceps, inserted through the catheter, may be used to pull the loop. After the catheter engages with the valve, the loop can optionally be released with the catheter remains engaged to inflate/deflate the balloon.

Additionally, as described, the check valve may be used in systems, methods, and environments other than a gastrointestinal balloon. The check valve in may have a string, or other extension, extending from the check valve. The string/extension may be grabbed by a tool inserted into the flow path to access the check valve.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A gastrointestinal balloon system, the gastrointestinal balloon system comprising:
   a gastrointestinal balloon;
   a valve located within the gastrointestinal balloon, the valve configured to allow fluid flow into and out of the gastrointestinal balloon;
   an attachment coupled to the valve, the attachment comprising an elongated member that extends into an opening of the gastrointestinal balloon and the valve, the elongated member having (i) a distal end that is coupled to the valve and (ii) a proximal end that comprises a connector that is disposed outside of the valve and the gastrointestinal balloon; and a shaft having a lumen, the lumen configured to receive a grasping tool, the elongated member, and the connector within an interior of the lumen, wherein the elongated member is configured as a guide that extends from a center of the valve within the gastrointestinal balloon to outside of the opening of the gastrointestinal balloon and the valve, in order to align the shaft with the valve and the gastrointestinal balloon, by receiving the elongated member and the connector within the interior of the lumen of the shaft, and wherein the grasping tool is configured to extend out a distal end of the shaft for grabbing the connector to align the shaft with the valve and the gastrointestinal balloon.

2. The gastrointestinal balloon system of claim 1, wherein the shaft is a catheter and the catheter has a tapered distal tip.

3. The gastrointestinal balloon system of claim 1, wherein the valve separates an interior of the gastrointestinal balloon with an exterior of the gastrointestinal balloon.

4. The gastrointestinal balloon system of claim 1, wherein the gastrointestinal balloon is configured to be inflated or deflated through the valve.

5. The gastrointestinal balloon system of claim 1, wherein the valve includes a proximal opening, a plunger, and an o-ring to seal an entry into the gastrointestinal balloon.

6. The gastrointestinal balloon system of claim 1, wherein the valve is a check valve.

7. The gastrointestinal balloon system of claim 1, wherein the elongated member is a string.

8. The gastrointestinal balloon system of claim 1, wherein the lumen is a central lumen of the shaft.

9. The gastrointestinal balloon system of claim 1, wherein the lumen is a single, central lumen of the shaft.

10. The gastrointestinal balloon system of claim 1, wherein the shaft is configured to extend into the opening of the gastrointestinal balloon and the valve.

11. The gastrointestinal balloon system of claim 10, wherein the system is configured to be positioned in (i) a first state in which the shaft is aligned with the valve, and the connector, at least a portion of the elongated member, and the grasping tool are positioned inside of the lumen of the shaft, and (ii) a second state in which the shaft extends into the opening of the gastrointestinal balloon and the valve, and the connector, at least a portion of the elongated member, and the grasping tool are still positioned inside of the lumen of the shaft.

12. The gastrointestinal balloon system of claim 1, wherein the valve has a central axis and the attachment extends into the valve along the central axis of the valve.

13. The gastrointestinal balloon system of claim 1, wherein the elongated member is at least one of a bungee, a stretchy member, a string, a cable, and a cord.

14. The gastrointestinal balloon system of claim 1, wherein the connector comprises at least one loop.

15. The gastrointestinal balloon system according to claim 1, wherein the valve located within the gastrointestinal balloon is configured without a protuberance on an exterior of the gastrointestinal balloon.

16. The gastrointestinal balloon system according to claim 1, wherein the grasping tool comprises at least one of forceps, a hinged arm, a hook, a rat-tooth grasper, a hook grasper, and a connection that aligns with the connector.

17. The gastrointestinal balloon system according to claim 1, further comprising the grasping tool.

18. The gastrointestinal balloon system according to claim 1, wherein the valve is a two-directional flow valve.

19. The gastrointestinal balloon system according to claim 1, wherein the grasping tool is configured to grasp and to release the connector.

20. A gastrointestinal balloon system, the gastrointestinal balloon system comprising:

a gastrointestinal balloon;

a valve located within the gastrointestinal balloon, the valve configured to allow fluid flow into and out of the gastrointestinal balloon; and an attachment coupled to the valve, the attachment comprising an elongated member that extends into an opening of the gastrointestinal balloon and the valve, the elongated member having (i) a distal end that is coupled to the valve and (ii) a proximal end that comprises a connector that is disposed outside of the valve and the gastrointestinal balloon, wherein the elongated member is configured as a guide that extends from a center of the valve within the gastrointestinal balloon to outside of the opening of the gastrointestinal balloon and the valve, in order to align a shaft with the valve and the gastrointestinal balloon, by receiving the elongated member and the connector within an interior of the shaft, and wherein a grasping tool is configured to extend out a distal end of the shaft for grabbing the connector to align the shaft with the valve and the gastrointestinal balloon.

21. The gastrointestinal balloon system according to claim 20, wherein the valve is a two-directional flow valve.

* * * * *